United States Patent
Wada et al.

(10) Patent No.: US 6,617,489 B2
(45) Date of Patent: Sep. 9, 2003

(54) ABSORBENT, ABSORBING PRODUCT BASED THEREON, AND WATER-ABSORBING RESIN

(75) Inventors: Katsuyuki Wada, Himeji (JP); Naoko Takahashi, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/846,180

(22) Filed: May 2, 2001

(65) Prior Publication Data

US 2002/0007170 A1 Jan. 17, 2002

(30) Foreign Application Priority Data

May 9, 2000 (JP) .................................. 2000-142243

(51) Int. Cl.[7] .............................................. A61F 13/15
(52) U.S. Cl. ........................ 604/368; 604/372; 523/111
(58) Field of Search ........................ 604/364, 367–368, 604/372; 523/111

(56) References Cited

U.S. PATENT DOCUMENTS

| | | |
|---|---|---|
| 4,626,252 A | 12/1986 | Nishizawa et al. |
| 4,654,039 A | 3/1987 | Brandt et al. |
| 5,061,259 A | 10/1991 | Goldman et al. |
| 5,147,343 A | 9/1992 | Kellenberger |
| 5,149,335 A | 9/1992 | Kellenberger |
| 5,204,061 A | 4/1993 | Covington et al. |
| 5,409,771 A | 4/1995 | Dahmen et al. |
| 5,422,405 A | 6/1995 | Dairoku et al. |
| 5,505,718 A | 4/1996 | Roe et al. |
| 5,599,335 A | 2/1997 | Goldman et al. |
| 5,601,542 A | 2/1997 | Melius et al. |
| 5,610,208 A * | 3/1997 | Dairoku et al. .......... 525/329.4 |
| 5,760,080 A | 6/1998 | Wada et al. |
| 5,762,641 A | 6/1998 | Bewick-Sonntag et al. |
| 5,797,893 A | 8/1998 | Wada et al. |
| 5,836,929 A | 11/1998 | Bewick-Sonntag et al. |
| 6,054,541 A | 4/2000 | Wada et al. |
| 6,068,924 A * | 5/2000 | Palumbo ..................... 428/402 |
| 6,184,433 B1 | 2/2001 | Harada et al. |

FOREIGN PATENT DOCUMENTS

| | | |
|---|---|---|
| EP | 0 532 002 A1 | 3/1993 |
| EP | 0 837 076 A2 | 4/1998 |
| EP | 0872491 | 10/1998 |
| EP | 0 884 037 A1 | 12/1998 |
| EP | 0 937 739 A2 | 8/1999 |
| EP | 0940148 | 9/1999 |
| EP | 1 072 630 A1 | 1/2001 |
| JP | 06-218007 | 8/1994 |
| JP | 11-099165 | 4/1999 |
| JP | 11-106536 | 4/1999 |
| JP | 11-106537 | 4/1999 |
| WO | WO 95/26209 | 10/1995 |
| WO | WO 00/10497 | 3/2000 |
| WO | WO 00/10498 | 3/2000 |
| WO | WO 00/10499 | 3/2000 |
| WO | WO 00/10501 | 3/2000 |

* cited by examiner

*Primary Examiner*—Weilun Lo
*Assistant Examiner*—C Lynne Anderson
(74) *Attorney, Agent, or Firm*—Nixon & Vanderhye, P.C.; Frank P. Presta

(57) ABSTRACT

The absorbent in accordance with the present invention is limited in at least two of the following requirements: ventilation resistance, absorbency under no load and/or under load, weight mean particle diameter, and water-soluble components. The absorbent exhibits a 24 g/g or more absorbency under a 2.0 kPa load and a 50 kPa·sec/m or less ventilation resistance under a 4.9 kPa load in a wet state. The absorbing product in accordance with the present invention is based on this absorbent and therefore exhibits improved ventilating properties when worn and relatively little wet back of water-based liquids, providing a further improved sense of comfort to users wearing the absorbing product.

19 Claims, 4 Drawing Sheets

ABSORBENT, ABSORBING PRODUCT BASED THEREON, AND WATER-ABSORBING RESIN

FIELD OF THE INVENTION

The present invention relates to absorbents that satisfactorily absorb body fluids and the like, absorbing products, such as disposable diapers, incontinence pads, and sanitary napkins, based on the absorbents, and water-absorbing resins preferably used for the absorbents and absorbing products.

BACKGROUND OF THE INVENTION

Conventional absorbing products, such as disposable paper diapers, incontinence pads, and sanitary napkins, has a basic structure of a top sheet, a back sheet, and an absorbent interposed between these sheets. The top sheet is permeable to liquid and touches the body of the user when he/she is in the product, thereby allowing body fluids to pass through it to the absorbent. The back sheet is impermeable to liquid and lies outside when he/she wears the product, thereby preventing the body fluids (water-based liquids) absorbed by the absorbent from leaking.

In such a situation, most back sheets, since having liquid impermeability, exhibit low gas permeability too. Therefore, vapor discharged from the body, as well as body fluids that have been absorbed and later evaporated due to body heat, cannot escape and accumulate between the absorbing product and the body. Consequently, a high humidity condition occurs where the absorbing product is being worn and causes a humid, sticky, or other unpleasant feel. If the product is worn for an extended period of time, it may cause a rash or other irritation to develop on the skin.

Accordingly, attempts have been made in the prior art to prevent an unpleasant feel and thereby improve the sense of comfort when the user is in the absorbing product, which are basically classified into the following three kinds of techniques.

The first kind is to improve on the back sheet. According to the technique, a high humidity condition is prevented from occurring by imparting ventilating properties to the back sheet with its liquid impermeability remaining intact.

Specific examples include Japanese Laid-Open Patent Application No. 58-149303/1983 (Tokukaisho 58-149303; published on Sep. 5, 1983) disclosing use, as the back sheet, of a liquid impermeable moisture-prevention sheet prepared by kneading polyolefin, a filling agent, and other materials, extending the mixture into a film, and forming microscopic pores; Japanese Laid-Open Patent Application No. 11-106536/1999 (Tokukaihei 11-106536; published on Apr. 20, 1999) disclosing use, as the back sheet, of a moisture permeable film prepared by extending a resin composition which contains minuscule particles of a filling agent and which is blended with cellulosic particles and forming pores in the extended resin composition; and Japanese Laid-Open Patent Application No. 11-106537/1999 (Tokukaihei 11-106537; published on Apr. 20, 1999) use, as the back sheet, of a moisture permeable film prepared by extending a resin composition which contains minuscule particles of a filling agent, which melts at a molding temperature, and which is blended with non-flowing polyolefin particles and forming pores in the extend resin composition.

The second kind is to provide a moisture absorbent. According to the technique, generated vapour is removed using moisture absorbent to prevent a high humidity condition from occurring. A specific example, among others, is Japanese Laid-Open Patent Application No. 6-218007/1994 (Tokukaihei 6-218007; published on Aug. 9, 1994) disclosing provision of a water-absorbing resin or other moisture absorbent in the absorbing product to prevent evaporation of body fluids.

Lastly, the third kind is to improve on the structure of the absorbing product. According to the technique, a high humidity condition is prevented from occurring by improving on the structure of the absorbing product and thereby preventing generation of vapor and encouraging dispersion of vapor. A specific example, among others, is Japanese Laid-Open Patent Application No. 11-99165/1999 (Tokukaihei 11-99165; published on Apr. 13, 1999) disclosing reducing the area where the absorbent touches the body to a minimum extent and creating a ventilating space between the absorbent and the body when the use is in the product by the use of a material that coats the absorbent.

All the foregoing techniques fall short of offering a sufficiently improved comfort when the user is in the absorbing product. Specifically, to prepare an absorbing product that provides a high level of comfort when worn, at least two problems need be addressed concurrently: (1) Absorbency under load must be raised to reduce "wet back," i.e., amounts of body fluid undesirably released after absorbed (elimination of a sticky feel). (2) The absorbent per se must possess improved ventilating properties (elimination of a humid feel). None of the techniques offers a sufficient level of solution to these problems.

Particularly, the absorbing product is spread over an expanded area since it absorbs the body fluid when it touches the body. Therefore, the absorbent as such, as well as the back sheet, acts as an air-tight separation wall having absorbed the body fluid and obstructs dispersion of vapor accumulated between the absorbing product and the body.

Without addressing the problem of the absorbent having absorbed the body fluid, etc. acting as an air-tight separation wall, no techniques, including the first to third techniques, can successfully solve problem (2) (elimination of a humid feel) and offer a sufficiently improved sense of comfort to the user in the absorbing product.

SUMMARY OF THE INVENTION

We, the inventors of the present invention, have diligently worked to solve these problems. Particularly, attention has been paid to the absorbent acting as an air-tight separation wall once it absorbs a body fluid or the like and changes to a wet state. As a result, we have found that the user feels more comfortable in the absorbing product if the absorbent has improved ventilating properties in a wet state and concurrently, the absorbed body fluid "wets back" the user only in reduced amounts, which has led to the completion of the invention.

In order to solve these problems, the absorbent in accordance with the present invention is characterized in that it has a 24 g/g or more absorbency under a 2.0 kPa load to physiological salt solution and a 50 kPa·sec/m or less ventilation resistance under a 4.9 kPa load in a wet state. The absorbent preferably contains a 40 weight percent or more water-absorbing resin and has a maximum basis weight of 700 g/m$^2$ or less.

Further, the absorbing product in accordance with the present invention is characterized in that it includes: an absorbing layer containing the absorbent; a liquid permeable sheet; and a liquid impermeable sheet having a ventilation resistance of not less than 1 kPa·sec/m and not more than 50 kPa·sec/m, the absorbing layer being disposed between the two layers.

In the conventional absorbent and absorbing product, no consideration is given to the ventilating properties of an absorbent per se in a wet state. Therefore, typical absorbents exhibit a high ventilation resistance of 100 kPa·sec/m or more in a wet state, which means that the absorbent, in practice, has no ventilating properties. Absorbents do exist that exhibit appreciable ventilating properties in a wet state. However, they cannot retain sufficient amounts of water-based liquid under load or sufficiently reduce the wet back of absorbed water-based liquid.

In contrast, in the present invention, the arrangement ensures excellent ventilating properties even when the absorbent or absorbing product is in a wet state and can prevent increases in wet back of absorbed water-based liquid. This prevents the absorbent from acting as an air-tight separation wall and a high humidity condition from building up between the body and the absorbent or the absorbing product, as well as enables the absorbent to sufficiently retain absorbed water-based liquid even under load. Hence, a humid feel and a sticky feel can be eliminated concurrently, enhancing the comfort the user feels when he/she is in the absorbing product.

An example of water-absorbing resin suitably used for the absorbent and absorbing product in accordance with the present invention is the one characterized in that it: possesses a ventilation resistance of 250 kPa·sec/m or less under a 4.9 kPa load in a wet state; has a 32 g/g or more absorbency under no load to physiological salt solution and a 32 g/g or more absorbency under a 2.0 kPa load to physiological salt solution; and is shaped in particles with a weight mean particle diameter of 430 μm or more.

Another example of water-absorbing resin suitably used for the absorbent and absorbing product in accordance with the present invention is the one characterized in that it: has a 250 kPa·sec/m or less ventilation resistance under a 4.9 kPa load in a wet state and a 34 g/g or more absorbency under no load to physiological salt solution; and comprises 18 weight percent or less water-soluble components.

A further example of water-absorbing resin suitably used for the absorbent and absorbing product in accordance with the present invention is the one characterized in that it: has a 250 kPa·sec/m or less ventilation resistance under a 4.9 kPa load in a wet state and a 34 g/g or more absorbency under a 2.0 kPa load to physiological salt solution; and comprises 18 weight percent or less water-soluble components.

In other words, the water-absorbing resin in accordance with the present invention satisfies an essential condition that it has a 250 kPa·sec/m or less ventilation resistance under a 4.9 kPa load in a wet state and one of first, second, or third groups of conditions: The first group of conditions is such that the water-absorbing resin has a 32 g/g or more absorbency under no load to physiological salt solution and a 32 g/g or more absorbency under a 2.0 kPa load to physiological salt solution and is shaped in particles with a weight mean particle diameter of 430 μm or more. The second group of conditions is such that the water-absorbing resin has a 34 g/g or more absorbency under no load to physiological salt solution and contains 18 weight percent or less water-soluble components. The third group of conditions is such that the water-absorbing resin has a 34 g/g or more absorbency under a 2.0 kPa load to physiological salt solution and contains 18 weight percent or less water-soluble components.

By using such a water-absorbing resin that satisfies these parameter requirements, the absorbent shows a ventilation resistance of 50 kPa·sec/m or less in a wet state and a 24 g/g or more absorbency under a 2.0 kPa load. The absorbing product based on the absorbent does not give a humid or sticky feel to evaluators, meaning that it creates a low humidity condition when worn. The water-absorbing resin can be thus suitably used for the absorbent and the absorbing product in accordance with the present invention.

Particularly, as mentioned earlier, the absorbent in accordance with the present invention preferably contains the water-absorbing resin with a ratio of 40 weight percent or more. This ensures that the absorbent does not act as an air-tight separation wall, prevents a humid feel and a sticky feel concurrently, and further enhances the comfort the user feels when he/she is in the absorbing product.

For a fuller understanding of the nature and advantages of the invention, reference should be made to the ensuing detailed description taken in conjunction with the accompanying drawings.

BRIEF DESCRIPTION OF DRAWINGS

Figure 1:
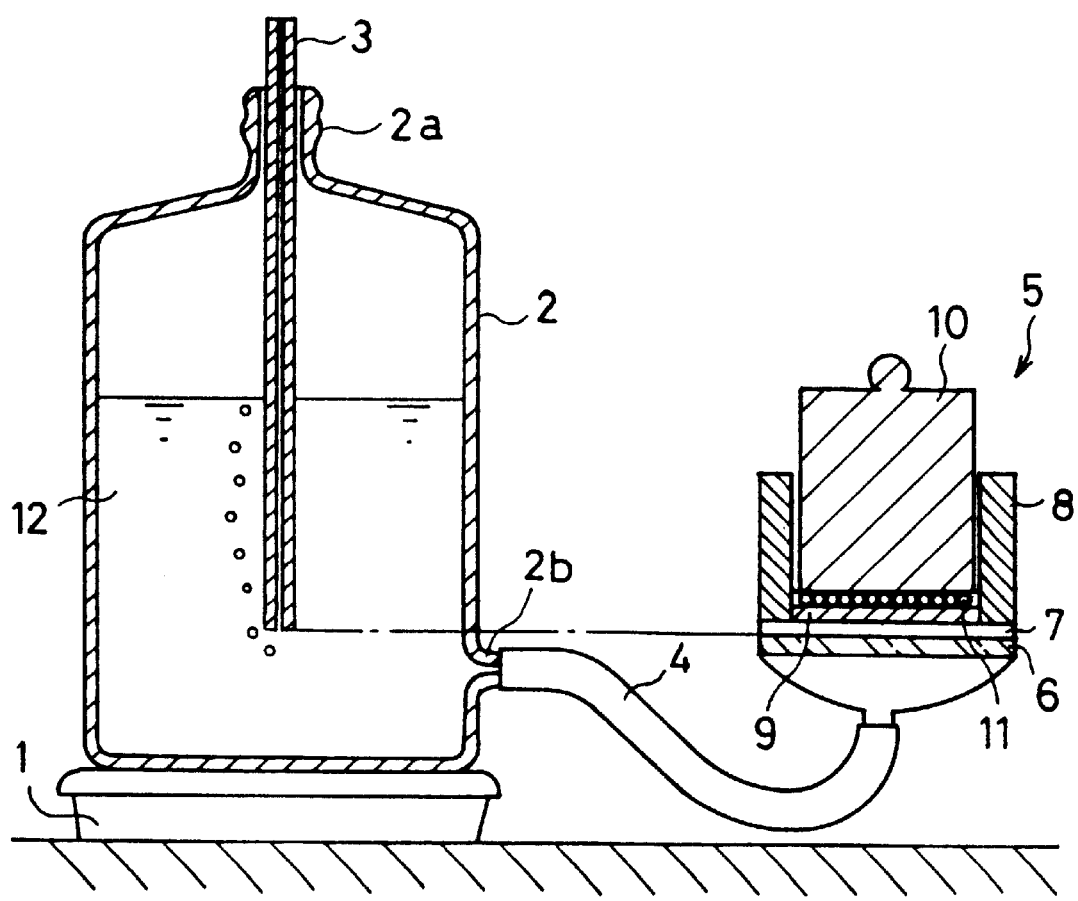
FIG. 1 is a cross-sectional view schematically showing an arrangement of a measurement instrument for absorbency under load, one of performances of the water-absorbing resin and absorbent in accordance with the present invention.

The following will describe an embodiment of the present invention; however, the description by no means limits the scope of the present invention.

An absorbent in accordance with the present invention can have at least satisfactory ventilating properties in a wet state in which water-based liquid is absorbed and a sufficient capability to retain absorbed water-based liquid under load.

The absorbent in the embodiments refers to a part of an absorbing product, such as a paper diaper or sanitary napkin, which is designed to absorb urine, blood, and other fluids. The absorbent is of a sheet shape with a thickness of typically not less than 0.1 mm and not more than 30 mm, preferably not less than 1 mm and not more than 10 mm, or of a substantially cylindrical shape; however, it may assume other shapes.

The absorbent is not limited in any particular manner in terms of its specific arrangement. Preferably, it contains a water-absorbing resin as a primary component for absorbing water and further contains fiber material, such as hydrophilic fiber.

The foregoing absorbents have one of following arrangements, to cite a few examples: (i) A water-absorbing resin is uniformly mixed with a fiber material. (ii) A water-absorbing resin is uniformly mixed with a fiber material. A layer is formed of the mixture, on which an additionally layer of a fiber material is deposited. (iii) A water-absorbing resin is uniformly mixed with a fiber material. A layer is formed of the mixture, between which and a layer of a fiber material there is interposed a water-absorbing resin. (iv) A water-absorbing resin is interposed between layers of a fiber material. Preferable among these examples is the arrangement whereby a water-absorbing resin is uniformly mixed with a fiber material because the arrangement is helpful in achieving the absorbency and ventilating properties of interest in the present invention.

Suitable examples of the fiber material include natural cellulose fibers, such as wooden mechanical, chemical, semi-chemical, and soluble pulps; artificial cellulose fibers, such as rayon and acetate; and hydrophilic fibers. Particularly suitable among them are natural cellulose fibers. The hydrophilic fibers may contain polyamide, polyester, polyolefin, and other synthetic fibers and other additional materials. The fiber material used for the absorbent in accordance with the present invention is not limited to those listed above.

In addition to the water-absorbing resin and the fiber materials, the absorbent in accordance with the present invention may contain other materials too. For example, if the absorbent contains relatively little fiber material, it may contain an adhesive binder to bind the fiber material together. As the fiber material is bound together by the adhesive binder, the absorbent is given an extra durability and capability to remain in shape before and after use.

Examples of the adhesive binder include thermal fusing fibers, such as polyethylene, polypropylene, ethylene-propylene copolymer, 1-butene-ethylene copolymer, and other polyolefin fibers; and adhesive emulsions. Any one of these adhesive binders may be used solo, or alternatively, any two or more of them may be used in combination. Preferably, the hydrophilic fiber and the adhesive binder are mixed with a ratio by weight of not less than 50/50 and not more than 99/1, more preferably not less than 70/30 and not more than 95/5, and even more preferably not less than 80/20 and not more than 95/5.

To the absorbent and water-absorbing resin can be added, for example, a deodorant, antimicrobial agent, perfume material, inorganic particles, foaming agent, chelating agent, pigment, dyeing material, hydrophilic short fiber, fertilizer, oxidizing agent, water, and salt, depending on the purpose in using the absorbent. The addition of these materials imparts a variety of functions to the absorbent and absorbing product including the absorbent.

The absorbent in accordance with the present invention may have an arrangement whereby arranged the water-absorbing resin is shaped in sheet by mixing the water-absorbing resin with a specified amount of water. Needless to say, various additional materials may be added in this arrangement too.

As mentioned earlier, in a wet state, the absorbent in accordance with the present invention has a ventilation resistance of 50 kPa·sec/m or less, preferably 40 kPa·sec/m or less, more preferably 30 kPa·sec/m or less, under a 4.9 kPa load. If the ventilation resistance in a wet state exceeds 50 kPa·sec/m, the absorbent acts as an air-tight separation wall. Especially, when such an inferior absorbent is used in an absorbing product such as a paper diaper, it causes a high humidity condition to occur between itself and the body, which deprives the user of much of the comfort he/she would otherwise feel wearing the product.

Note that in the present invention the absorbent's ventilation resistance is measured by a method detailed in a section "Ventilation Resistance of Absorbent under Load in Wet State" in an embodiment described later. The above ranges of ventilation resistances were obtained from measurements using this method.

The absorbent in accordance with the present invention has a 24 g/g or more absorbency under load, preferably 26 g/g or more, more preferably 28 g/g or more, to physiological salt solution under a 2.0 kPa load. If the absorbency under load is less than 24 g/g, the absorbed liquid is not retained sufficiently by the absorbent and seeps out due to load (body weight of the user). Such an inferior absorbent in a paper diaper and other absorbing products causes a sticky feel, and a rash may develop after hours of prolonged use, which deprives the user of much of the comfort he/she would otherwise feel wearing the product. It was found that the absorbency under load is equivalent to the amount of a water-based liquid being retained in 1 g of an absorbent when the absorbent is subjected to a load under prescribed conditions and that the absorbency under load is related to results of evaluation as will be described in embodiments below. The conditions in measurement of absorbency under load and the composition of artificial urine will be detailed later in an embodiment.

In the absorbent in accordance with the present invention, the "wet back," i.e., the amount of fluid undesirably seeping out after being absorbed by the absorbent, is preferably reduced to a minimum level possible under load. Preferable ranges of the wet back are not prescribed in a specific manner, since they can vary depending on the purpose of using the absorbent, that is, the type and shape of the absorbing product.

As mentioned earlier, the absorbent in accordance with the present invention contains a water-absorbing resin as a primary component. The water-absorbing resin preferably accounts for 40 weight percent or more, more preferably 50 weight percent or more, even more preferably 60 weight percent or more, further more preferably 70 weight percent or more, of the absorbent in accordance with the present invention. For upper limits, the water-absorbing resin preferably accounts for 100 weight percent or less, more preferably 97 weight percent or less, even more preferably 95 weight percent or less, of the absorbent in accordance with the present invention. If the water-absorbing resin accounts for less than 40 weight percent, the fiber material accounts for too great a portion and reduces the absorbency under load, etc. A possible result is that the user feels less comfortable wearing an absorbing product based on such a water-absorbing resin.

The absorbent preferably has a maximum basis weight (basis weight of the absorbent where it is thickest) of 700 $g/m^2$ or less, more preferably 600 $g/m^2$ or less, and even more preferably 500 $g/m^2$ or less. If the absorbent's maximum basis weight exceeds 700 $g/m^2$, the absorbent becomes unnecessarily thick or heavy and in some cases fails to provide an adequate level of comfort to the user in an absorbing product based on such an absorbent.

To accomplish the objective of the present invention to deliver a high level of comfort to the user wearing the absorbing product, at least two requirements need be met concurrently: (1) Absorbency under load must be raised to reduce wet back (elimination of a sticky feel). (2) The absorbent per se must possess improved ventilating properties (elimination of a humid feel).

If the absorbent contains as primary components a water-absorbing resin and a fiber material, the ratio of the water-absorbing resin to the absorbent needs be increased to fulfill requirement (1). However, with too great a ratio of the water-absorbing resin, the ventilating properties of the absorbent degrade. Conversely, to fulfill requirement (2), the ratio of the fiber material to the absorbent needs be increased. However, with too great a ratio of the fiber material, the absorbency under load drops and the wet back increases.

Accordingly, the water-absorbing resin suitably used for the absorbent in accordance with the present invention has a ventilation resistance 250 kPa·sec/m or less, preferably 200 kPa·sec/m or less, more preferably 150 kPa·sec/m or less, even more preferably 100 kPa·sec/m or less, still more preferably 50 kPa·sec/m or less under a 4.9 kPa load in a wet state, exhibits an absorbency of 32 g/g or more, preferably 34 g/g or more, more preferably 36 g/g or more, both under a 2.0 kPa load and under no load to physiological salt solution, and is composed of particles with a weight mean particle diameter of 400 $\mu$m or more, preferably 430 $\mu$m or more, more preferably 450 $\mu$m or more, of which 5 weight percent or less, preferably 3 weight percent or less, more preferably 1 weight percent or less, have a diameter of less than 106 $\mu$m. In addition, the water-soluble components account for 18 weight percent or less, preferably 14 weight percent or less, more preferably 10 weight percent or less, of the water-absorbing resin.

Further, the water-absorbing resin exhibits an absorbency of preferably 24 g/g or more, more preferably 26 g/g or more, even more preferably 28 g/g or more, under a load as high as 4.9 kPa to physiological salt solution. Under the equal load of 4.9 kPa, to artificial urine, the water-absorbing resin exhibits an absorbency of preferably 30 g/g or more, more preferably 32 g/g or more, even more preferably 34 g/g or more. The water-absorbing resin has a bulk specific gravity and solid components in the range of that of the precursor detailed later.

If the water-absorbing resin has an excessively high ventilation resistance in a wet state, the resin, when incorporated as an absorbent, especially at a high ratio, fails to fulfill requirement (2), since it cannot provide sufficient ventilation in actual use. If the absorbency is too low under no load and under load, requirement (1) is not fulfilled, since the absorbent can neither absorb sufficient amounts of water-based liquid nor retain absorbed liquid therein under load. If the water-absorbing resin has too small a weight mean particle diameter with too many minuscule particles having a diameter of less than 106 $\mu$m, requirement (2) is not fulfilled, since the absorbent, when having absorbed water-based liquid and gelled, does not have spaces between gelled particles and fails to deliver satisfactory ventilating properties.

Another technique to fulfill requirement (2) is to enhance gel strength. However, this is not preferable because an increased gel strength normally causes the absorbency under no load to drop. Meanwhile, with too great an absorbency under no load, requirement (2) cannot be fulfilled, since gel strength deteriorates, and gelled particles are not spaced apart from one another. With excessive amounts of water-soluble components contained in the water-absorbing resin, requirement (2) cannot be again fulfilled, since the water-absorbing resin absorbs water-based liquid and gels, and dissolved water-soluble components clog gelled particles and degrade ventilation to a less-than-satisfactory level.

To summarize the description above, the inventors have found that in a water-absorbing resin suitably used for an absorbent of which 40 weight percent or more is the water-absorbing resin, it is important to strike a good balance among absorbency under no load, absorbency under load, weight mean particle diameter, amounts of minuscule particles with a diameter of less then 106 $\mu$m, and amounts of water-soluble components.

Therefore, by using the water-absorbing resin in accordance with the present invention, an absorbent can be obtained that absorbs water-based liquid sufficiently, wets back the user only in reduced amounts even under load, and deliver satisfactory ventilating properties. Thus, this absorbent surely satisfies both requirements (1) and (2) and provides an increased sense of comfort to the user when incorporated in absorbing products, as compared to conventional absorbents.

Conditions in measurement of absorbency under no load and under load, as well as ventilation resistance, amounts of water-soluble components, and weight mean particle diameter of the water-absorbing resin will be detailed later in embodiments.

Measuring using a bulk specific gravity measurement instrument (manufactured by Kuramochi Scientific Instrument), the water-absorbing resin precursor exhibits a bulk specific gravity of not less than 0.55 g/ml and not more than 0.85 g/ml, preferably not less than 0.60 g/ml and not more than 0.80 g/ml, more preferably not less than 0.65 g/ml and not more than 0.75 g/ml. The water-absorbing resin precursor possesses an absorbency under no load of not less than 35 g/g and not more than 50 g/g, preferably not less than 37 g/g and not more than 48 g/g, to physiological salt solution and contains 18 weight percent or less water-soluble components, preferably not less than 5 weight percent and not more than 18 weight percent, and further contains solid components in a range of not less than 90 weight percent and not more than 100 weight percent, preferably not less than 91 weight percent and not more than 99 weight percent, preferably not less than 92 weight percent and not more than 98 weight percent.

If the bulk specific gravity is less than 0.55 g/ml, undesirable problems may arise where properties degrade due to difficulties in mixing a surface crosslinking agent (detailed later) and transportation cost increases due to decreases in the weight per unit volume. If the bulk specific gravity is more than 0.85 g/ml, it may become difficult to provide sufficient ventilation between gelled particles.

If the water-absorbing resin precursor possesses an absorbency under no load of less than 35 g/g to physiological salt solution, the absorbency under no load after surface crosslinking drops (detailed later), causing the absorbent to undesirably wet back much. If the absorbency under no load exceeds 50 g/g, when the water-absorbing resin has absorbed a water-based solution and gelled, the gelled particles are in some cases deformed much due to pressure and clogged by water-soluble components originally in the gel, but now dissolved. The result is undesirably low ventilation.

If the water-absorbing resin precursor contains excessive amounts of water-soluble components, when the water-absorbing resin has absorbed a water-based solution and gelled, the gelled particles are clogged by the water-soluble components originally in the gel, but now dissolved. The result is again undesirably low ventilation.

If the solid components account for less than 90 weight percent, aggregation is likely to occur during surface crosslinking. This interrupts the water-absorbing resin precursor from mixing well with a surface crosslinking agent and undesirably makes it difficult to impart expected properties by means of surface crosslinking.

Conditions in measurement of bulk specific gravity and solid components will be detailed later in embodiments.

The water-absorbing resin in accordance with the present invention is generally fabricated by crosslinking the surface of a water-absorbing resin precursor. The water-absorbing resin precursor is composed of resin particles with a weight mean particle diameter of 400 μm or more, more preferably 430 μm or more, of which 5 weight percent or less, preferably 1 weight percent or less, have a diameter of less than 106 μm, and contains carboxyl groups that form a hydrogel by absorbing large amounts of water.

The water-absorbing resin precursor is synthesized, for example, by water solution polymerization or inverse phase suspension polymerization, preferably by water solution polymerization. Specific examples of the water-absorbing resin precursor include crosslinked products of partially neutralized polyacrylic acids, hydrolysis products of starch-acrylonitrile graft polymers, neutralized products of starch-acrylic acid graft polymer, saponified products of vinyl acetate-acrylic acid ester copolymers, hydrolysis or crosslinked products of acrylonitrile or acrylamide copolymers, denatured products of crosslinked polyvinyl alcohols containing carboxyl groups, and crosslinked isobutylene-maleic anhydride copolymers.

The water-absorbing resin precursor is prepared by polymerizing or copolymerizing one or more monomers selected from the group consisting of unsaturated carboxylic acids, such as (meth)acrylic acid, maleic acid, maleic anhydride, fumaric acid, crotonic acid, itaconic acid, and β-acryloyloxypropionic acid, and neutralized products of these acids, subjecting the monomer to grinding, classification, and other operations as required to obtain particles with the aforementioned weight mean particle diameter. Preferred among the monomers are (meth)acrylic acids and their neutralized products.

The water-absorbing resin precursor may be a copolymer of one of the monomers and another monomer that can be copolymerizable with the monomer. Specific examples of the other monomer includes anionic unsaturated monomers, such as vinyl sulfonic acid, styrene sulfonic acid, 2-(meth)acrylamide-2-methylpropane sulfonic acid, 2-(meth)acryloylethane sulfonic acid, and 2-(meth)acryloylpropane sulfonic acid, and their salts; nonionic hydrophilic-group-containing unsaturated monomers, such as acrylamide, methacrylamide, N-methyl(meth)acrylamide, N-ethyl(meth)acrylamide, N-n-propyl (meth) acrylamide, N-isopropyl (meth) acrylamide, N,N-dimethyl (meth)acrylamide, 2-hydroxyethyl(meth)acrylate, 2-hydroxypropyl (meth) acrylate, methoxypolyethylene glycol (meth) acrylate, polyethylene glycol mono (meth) acrylate, vinylpyridine, N-vinylpyrolidone, N-acryloylpiperidine, and N-acryloylpyrrolidine; cationic unsaturated monomers, such as N,N-dimethylaminoethyl(meth)acrylate, N,N-diethylaminoethyl(meth)acrylate, N,N-dimethylamino propyl(meth)acrylate, and N,N-dimethylamino propyl (meth)acrylamide, and their quaternary salts.

The content of carboxyl groups in the water-absorbing resin precursor is not limited in any particular manners; however, a 0.01 or more equivalent amount of carboxyl groups are preferably contained in every 100 g of the water-absorbing resin precursor. If the water-absorbing resin precursor is, for example, a crosslinked product of partially neutralized polyacryl acid, the unneutralized polyacrylic acid preferably accounts for 1 mole percent to 60 mole percent, more preferably 10 mole percent to 50 mole percent, even more preferably 20 mole percent to 40 mole percent, of the crosslink. The neutralization may be performed with either a monomer or a polymer, or both. Carboxyl groups are neutralized with an alkaline metal salt and/or ammonium salt, preferably with an alkaline metal salt. Particularly preferred among alkaline metal salts are sodium salt, potassium salt, and lithium salt.

Preferably, the water-absorbing resin precursor is internally crosslinked by being reacted or copolymerized with a crosslinking agent (interior crosslinking agent) containing polymerizing unsaturated groups and reactive groups. The water-absorbing resin precursor may be self-crosslinking and does not need a crosslinking agent.

Specific examples of the crosslinking agent include N,N'-methylene-bis(meth)acrylamide, (poly)ethyleneglycol di(meth)acrylate, (poly)propylene glycol di(meth)acrylate, trimethylolpropane di(meth)acrylate, trimethylolpropane tri(meth)acrylate, glycerol tri(meth)acrylate, glycerol acrylate methacrylate, ethylene-oxide-denatured trimethylolpropane tri (meth) acrylate, pentaerythritol tetra (meth) acrylate, dipentaaerythritol hexa(meth)acrylate, triallyl cyanurate, triallyl isocyanurate, triallyl phosphate, triallyl amine, poly (meth)allyloxyalkane, (poly)ethylene glycol diglycidyl ether, glycerol diglycidyl ether, ethylene glycol, polyethylene glycol, propylene glycol, glycerol, pentaerythritol, ethylenediamine, polyethylene imine, and glycidyl (meth) acrylate.

Any one of these crosslinking agents may be used solo, or alternatively, any two or more of them may be used in combination. Among the compounds listed as examples, two or more compounds containing polymerizing unsaturated groups are preferably used in combination as crosslinking agent in the present invention.

The crosslinking agent is used at preferably 0.005 mole percent to 2 mole percent, more preferably 0.05 mole percent to 1 mole percent, to the total amount of the monomer. If the crosslinking agent is used at less than 0.005 mole percent, an inflating gel of the water-absorbing resin undesirably becomes less stable to urine and other body fluids.

Apart from the monomers and crosslinking agents, hydrophilic high polymers (starch, polyvinyl alcohol, polyacrylic acid (acrylate), and/or their crosslinked product, etc.), foaming agents, chain moving agents, surface activating agents, and chelating agents may be added in the polymerization as required.

When initiating polymerization in the polymerization reaction, radical polymerization initiators, such as potassium persulfate, ammonium persulfate, sodium persulfate, t-butylhydroperoxide, hydrogen peroxide, and 2,2'-azobis(2-amidinopropane) dihydrochloride salt, or active energy beams, such as ultraviolet and electron beams, may be used for example. If an oxidizing radical polymerization initiator is to be used, redox polymerization may be performed using a reducing agent, such as, sodium sulfite, sodium hydrogensulfite, ferrous sulfate, or L-ascorbic acid, together with the initiator. The polymerization initiators are used at preferably 0.001 mole percent to 2 mole percent, more preferably 0.01 mole percent to 0.5 mole percent to the total amount of the monomer.

The polymerization is carried out normally in the form of water solution. The solid components used in the polymerization account for not less than 10 weight percent and not more than 80 weight percent, preferably not less than 20 weight percent and not more than 70 weight percent, more preferably not less than 30 weight percent and not more than 65 weight percent, of the monomer.

If the resultant polymer from the polymerization is a water-containing gel, the polymer is dried, ground, and classified as required to obtain water-absorbing resin precursor.

The drying process is carried out at not less than 80° C. and not more than 250° C., preferably not less than 150° C. and not more than 200° C., until the solid components reach the aforementioned ratios. Specific methods are not limited in any particular manners; suitable examples include azeotropic dehydration, fluidized drying, and stationary heated air drying. Particularly preferred among them is stationary heated air drying.

The absorbency under load of the water-absorbing resin precursor typically does not fall in the preferred range for the present invention (32 g/g or more) Accordingly, by using a specified surface crosslinking agent, the crosslink density needs be raised near the surface, relative to the interior, of the water-absorbing resin precursor. In other words, the water-absorbing resin in accordance with the present invention is obtainable by crosslinking the surface and its proximity of the water-absorbing resin precursor with a specified surface crosslinking agent.

Specifically, the water-absorbing resin in accordance with the present invention is obtainable by modifying the water-absorbing resin precursor obtained from water solution polymerization or inverse phase suspension polymerization, preferably from the aforementioned water solution polymerization, by classification and other operations so that the weight mean particle diameter is not less than 400 μm and not more than 850 μm, preferably not less than 430 μm and not more than 850 μm, more preferably not less than 450 μm and not more than 850 μm, and also that 5 weight percent or less of the precursor have a diameter of less than 106 μm, and subsequently heating the modified precursor in the presence of a surface crosslinking agent. The resultant water-absorbing resin shows a 32 g/g or more absorbency under no load and under a 2.0 kPa load to physiological salt solution and has a weight mean particle diameter of 400 μm or more, more preferably 430 μm or more, even more preferably 450 μm or more.

The water-absorbing resin precursor may be fabricated into a predetermined shape or may assume spherical, scalelike, randomly crushed, granular, and other various shapes. Further, the water-absorbing resin precursor may be primary particles, granulated products of those primary particles, or a mixture. If the weight mean particle diameter is less than 400 μm or if those particles with a diameter of less than 106 μm account for more than 5 weight percent, the water-absorbing resin or absorbent with satisfactory parameters in accordance with the present invention may not be obtained.

The surface crosslinking agent may be one of various known crosslinking agents and is not limited in any particular manners. However, two kinds of crosslinking agents (a first surface crosslinking agent and a second surface crosslinking agent) with different solubility parameters (SP values) are preferably used in combination. This is because such a combination better allows conditions in the soaking of the crosslinking agent into the water-absorbing resin surface and the thickness of the crosslink to be selected freely. Particularly, a water-absorbing resin with an excellent absorbency under load, and hence a water-absorbing resin with excellent ventilation, become readily obtainable in accordance with the present invention.

The solubility parameter is a value typically used as a factor to indicate the polarity of a compound. In the present invention, the inventors employed the values of the solubility parameter, $\delta(J/m^3)^{1/2}$, i.e., $(cal/cm^3)^{1/2}$, as described for various solvents in *Polymer Handbook*, $3^{rd}$ Ed., pages 527–539, published by Wiley Interscience. The solubility parameters of those solvents that cannot be found in the pages were calculated by substituting Hoy's concentrated energy constant in page 525 to Small's Equation in page 524 of the same book.

The first surface crosslinking agent is preferably a compound that can react with carboxyl groups and that has a solubility parameter of $2.56 \times 10^4 \ (J/m^3)^{1/2}$ or more, i.e., 12.5 $(cal/cm^3)^{1/2}$ or more, more preferably of $2.66 \times 10^4 \ (J/m^3)^{1/2}$ or more, i.e., 13.0 $(cal/cm^3)^{1/2}$ or more. Specific examples of the first surface crosslinking agent include ethylene glycol, propylene glycol, glycerol, pentaerythritol, soribitol, ethylene carbonate (1,3-dioxolane-2-on), and propylene carbonate (4-methyl-1,3-dioxolane-2-on). However, other compounds may be used instead. Any one of these first surface crosslinking agents may be used solo, or alternatively, any two or more of them may be used in mixture.

The second surface crosslinking agent is preferably a compound that can react with carboxyl groups and that has a solubility parameter of less than $2.56 \times 10^4 \ (J/m^3)^{1/2}$, i.e., less than 12.5 $(cal/cm^3)^{1/2}$, more preferably not less than $2.02 \times 10^4 \ (J/m^3)^{1/2}$ and not more than $2.46 \times 10^4 \ (J/m^3)^{1/2}$, i.e., not less than 9.5 $(cal/cm^3)^{1/2}$ and not more than 12.0 $(cal/cm^3)^{1/2}$. Specific examples of the second surface crosslinking agents include diethylene glycol, triethylene glycol, 1,3-propanediol, 1,4-butanediol, 1,5-pentanediol, 2,4-pentanediol, 1,6-hexanediol, 2,5-hexanediol, trimethylolpropane, diethanolamine, triethanolamine, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, ethylenediamine, diethylenetriamine, triethylenetetramine, 2,4-tolylenediisocyanate, hexamethylene diisocyanate, 4,5-dimethyl-1,3-dioxolane-2-on, epichlorohydrin, and epibromohydrin. However, other compounds may be used instead. Any one of these second surface crosslinking agents may be used solo, or alternatively, any two or more of them may be used in mixture.

The first and second surface crosslinking agents are used at preferably 0.01 parts by weight to 5 parts by weight and 0.001 parts by weight to 1 part by weight, more preferably 0.1 parts by weight to 2 parts by weight and 0.005 parts by weight to 0.5 parts by weight, respectively for every 100 parts by weight of the solid components of the water-absorbing resin precursor. However, the amount(s) of the surface crosslinking agent(s) used is(are) variable depending on the kind of compound used and combination.

The use of the aforementioned surface crosslinking agents can raise the crosslink density of the water-absorbing resin precursor, i.e., the crosslink density near the surface, relative to the interior, of the water-absorbing resin precursor and increase the absorbency under load to a sufficiently high value which is required to the water-absorbing resin in accordance with the present invention. Using the surface crosslinking agents at more than 10 parts by weight is not only uneconomical, but also not desirable in terms of formation of a most suitable crosslinking structure in the water-absorbing resin, because an excessive amount of surface crosslinking agents causes the absorbency under no load to fall. Using the surface crosslinking agents at less than 0.001 parts by weight is not desirable either, because the water-absorbing resin fails to shows an expected improvement in its absorbency under load.

The water-absorbing resin precursor is mixed with the surface crosslinking agent(s) preferably in water serving as a solvent. Water is added at preferably more than 0 and 20 parts by weight or less, more preferably 0.5 parts by weight to 10 parts by weight for every 100 parts by weight of the solid components of the water-absorbing resin precursor. However, the amount of water used is variable depending on the particle diameter and kind of water-absorbing resin precursor.

In the present invention, preferable surface crosslinking agents are polyhydric alcohols, particularly, polypropylene glycol. The use of a polyhydric alcohol improves properties further, as well as enables the absorbent to be better sustained in shape and allows easy molding in the manufacture of the absorbent.

The water-absorbing resin precursor may be mixed with the surface crosslinking agent(s) in a hydrophilic organic solvent as required. Examples of the hydrophilic organic solvents include lower alcohols, such as methanol, ethanol, 1-propanol, 2-propanol, 1-butanol, 2-butanol, and t-butanol (2-methyl-2-propanol); ketones, such as acetone; ethers, such as dioxane and tetra hydrofuran; amides, such as N,N-dimethyl formamide; and sulfoxides, such as dimethyl sulfoxide. The hydrophilic organic solvent is used at preferably 20 parts by weight or less, more preferably 0.1 parts by weight to 10 parts by weight, for every 10 parts by weight of the solid components of the water-absorbing resin precursor. However, the amount of the hydrophilic organic solvent is variable depending on the particle diameter and kind of water-absorbing resin precursor.

The surface crosslinking agents may be mixed with the water-absorbing resin precursor after dispersing the water-absorbing resin precursor in the hydrophilic organic solvent, for example. However, the method of mixture is not limited in any particular manners. Preferred among many a mixing method is that whereby the surface crosslinking agents are sprayed or dropped directly to water and/or the water-absorbing resin precursor as required to form a mixture.

A particularly preferred method to impart improved properties is to spray a surface crosslinking agent to a water-absorbing resin precursor that is being stirred at high speed. The stirring is carried out at a rate of 300 rpm or more, preferably not less than 1000 rpm and not more than 3000 rpm. The surface crosslinking agent is sprayed to form mist of not less than 100 μm and not more than 500 μm, preferably not less than 200 μm and not more than 400 μm.

In the mixing process, at least one of the mixing temperatures, i.e., the temperature of the water-absorbing resin precursor before mixing and that of the surface crosslinking agent, is preferably specified in a certain range. The specification facilitates the control of the thickness of the surface activating layer formed by the surface crosslinking agent and makes it easier to exploit the performance of the water-absorbing resin of the present invention. The temperature of the water-absorbing resin precursor before mixing is generally not less than 0° C. and not more than 100° C., preferably not less than 60° C. and not more than 80° C., more preferably not less than 60° C. and not more than 75° C., and even more preferably not less than 60° C. and not more than 70° C.

If the temperature of the water-absorbing resin precursor before adding a water solution is too high, it does not uniformly mix with the surface crosslinking agent; if is too low, the powders (i.e., water-absorbing resin precursor) aggregate, which is undesirable. The temperature of the surface crosslinking agent is not less than 5° C. and not more than 45° C., preferably not less than 10° C. and not more than 40° C., more preferably not less than 15° C. and not more than 35° C. Since some surface crosslinking agents possibly contain volatile components (components with low flashing points), setting the temperature of the surface crosslinking agent to a high temperature is not desirable for safety reasons.

If water is used to mix the water-absorbing resin precursor with a surface crosslinking agent, fine particle powders, surface activating agents, etc. that do not dissolve in water may coexist in the water.

A mixer for use in mixing the water-absorbing resin precursor and the surface crosslinking agents is preferably equipped with a powerful mixing force to mix the ingredients certainly and uniformly. Preferred examples of the mixer include a cylindrical mixer, a double-walled conical mixer, a V-shaped mixer, a ribbon mixer, a screw mixer, a flow furnace rotary desk mixer, a gas flow mixer, a double-armed kneader, an internal mixer, a grind kneader, a rotary mixer, and a screw extruder.

After mixing the water-absorbing resin precursor with the surface crosslinking agents, the resultant mixture is processed with heat to form crosslinks near the surface of the water-absorbing resin precursor. The process is carried out preferably at 100° C. to 250° C., more preferably at 120° C. to 250° C., even more preferably at 160° C. to 250° C. (the temperature of a heat source for heating or that of the heated precursor, preferably the temperature of a heat source for heating). However, the temperature is variable depending on the surface crosslinking agents used. Using a processing temperature of less than 100° C. is not desirable, because a uniform crosslinking structure cannot be obtained and therefore a water-absorbing resin with an excellent dispersion absorbency and other performance cannot be obtained. Using a processing temperature of more than 250° C. is not desirable either, because the water-absorbing resin precursor degrades and the resultant water-absorbing resin shows poor performance.

The heat treatment can be carried out using a normal drier and or heating furnace. Examples of driers include groove-type mixture driers, rotary driers, desk driers, fluidized bed driers, gas flow driers, and infrared driers.

Materials may be added to the water-absorbing resin in accordance with the present invention obtained in this manner as required either during manufacture or after manufacture, including a deodorant, perfume material, inorganic particles, foaming agent, pigment, dyeing material, antimicrobial agent, hydrophilic short fiber, molding agent, adhesive agent, surface activating agent, fertilizer, oxidizing agent, reducing agent, chelating agent, water, and salt. The addition of these materials imparts a variety of functions to the water-absorbing resin.

The inorganic particles are not limited in any particular manners, as long as they are inactive to water-based liquids and the like. Examples include fine particles of various inorganic compounds and clay minerals. Especially preferred inorganic particles are those with a sufficient hydrophilic property and no or low solubility to water. Specific examples include metal oxides, such as silicon dioxide and titanium oxides; silicic acids (silicates), such as natural and synthetic zeolite; kaolin, talc, clay, and bentonite. Especially preferred among these are silicon dioxide and silicic acids (silicates). It would be further preferable if silicon dioxide or silicic acids (silicates) have a mean particle diameter of 200 μm measured by a coal tar counter method.

The inorganic particles may used normally at amounts of not less than 0.001 parts by weight and not more than 10 parts by weight, preferably not less than 0.01 parts by weight and not more than 5 parts by weight, per 100 parts by weight of the water-absorbing resin in accordance with the present invention. The mixing method of the water-absorbing resin and the inorganic particles is not limited in any particular manners. Examples of the method include dry blend and wet mixing; particularly preferred is a dry blend method.

The water-absorbing resin in accordance with the present invention is typically obtainable by crosslinking the surface of the water-absorbing resin precursor. The water-absorbing resin precursor exhibits a bulk specific gravity of not less than 0.55 g/ml and not more than 0.85 g/ml, contains solid components in a range of not less than 90 weight percent and not more than 100 weight percent, possesses an absorbency under no load of not less than 35 g/g and not more than 50 g/g to physiological salt solution, contains 18 weight percent or less water-soluble components, has a weight mean particle diameter of 400 $\mu$m or more, and contains 5 weight percent or less particles having a weight mean particle diameter of less than 106 $\mu$m. In addition, a surface crosslinking agent specified not less than 5° C. and not more than 45° C. is added by means of spraying to the water-absorbing resin precursor specified not less than 0° C. and not more than 100° C., preferably not less than 60° C. and not more than 75° C., and the surface is crosslinked through a heat treatment to obtain the water-absorbing resin in accordance with the present invention. The surface crosslinking agent preferably contains a polyhydric alcohol, more preferably polypropylene glycol.

The absorbing product in accordance with the present invention, based on the foregoing water-absorbing resin, is constructed of an absorbing layer containing the absorbent arranged as above, the layer being interposed between a top sheet (front sheet) and a back sheet (bottom sheet). Specific examples of the absorbing product includes paper diapers (disposable diapers), sanitary napkins, so-called incontinence pads, and other sanitary articles, but are not limited to these. Absorbing products have excellent water-absorbing properties. For example, a paper diaper can prevent leakage of urine and deliver a dry feel (detailed late).

As the top sheet (hereinafter referred to as a liquid permeable sheet) is used a sheet that is permeable to water-based liquids (liquid permeable properties). The liquid permeable sheet may be fabricated from any material, as long as the material is permeable to water-based liquids. Examples of such a material include non-woven fabric; woven fabric; porous synthetic resin films made of polyethylene, polypropylene, polyester, or polyamide.

As the back sheet (hereinafter referred to as a liquid impermeable sheet) is used a sheet that is impermeable to water-based liquids and highly ventilating (detailed late). The liquid impermeable sheet may be fabricated from any material, as long as the material is impermeable to water-based liquids. Examples of such a material include synthetic resin films made of polyethylene, polypropylene, ethylene vinyl acetate, and polyvinyl chloride; films made of composite material of such a synthetic resin and non-woven fabric; and films made of composite materials of such a synthetic resin and woven fabric.

The film is subjected to various processing to ensure that it has ventilating properties. The method is not limited in any particular manners. A suitable example is a method whereby the film is elongated at least in one direction before being provided with microscopic pores.

The ventilation resistance of the liquid impermeable sheet is preferably in a range from 1 kPa·sec/m to 50 kPa·sec/m, more preferably from 1 kPa·sec/m to 40 kPa·sec/m, even more preferably from 1 kPa·sec/m to 30 kPa·sec/m. If the ventilation resistance is less than 1 kPa·sec/m, the ventilating properties are too good and the sheet's performance as a liquid impermeable back sheet becomes poor. Meanwhile, if the ventilation resistance exceeds 50 kPa·sec/m, the ventilating properties are too poor, the improved ventilating properties of the absorbent are wasted. The ventilation resistance of the liquid impermeable sheet is measured when the sheet is practically dry. The ranges of the ventilation resistance are obtained from measurements under these conditions.

The arrangement of the absorbing layer is not limited in any particular manners, as long as it contains the foregoing absorbent. Accordingly, the absorbing layer contains materials other than the absorbent as required depending on the kind of absorbing product and its use. Manufacturing methods of the absorbing layer are not limited in any particular manners either. Besides, a dispersion layer may be disposed on the top surface of the absorbing layer, the back surface of the back sheet, or the top surface of the top sheet. The dispersion layer helps the liquid absorbed by the absorbing layer disperse to enable the absorbent to absorb the liquid more efficiently and quickly. The dispersion layer may be fabricated from any material as long as the material helps the liquid to disperse. Examples include layers having non-woven fabric, cellulose, crosslink cellulose as a primary component.

Methods of interposing the absorbing layer between the top sheet and the back sheet, i.e., manufacturing methods of the absorbing product, are not limited in particular manners. If paper diapers are to be manufactured as the absorbing product, conventional methods for paper diapers are applicable. If sanitary napkins are to be manufactured as the absorbing product, conventional methods for sanitary napkins can be suitably applied.

If the absorbing product in accordance with the present invention is used as sanitary articles absorbing body fluids, the product can provide pleasantly dry feels, wherein it does not give a humid feel due to high humidity, a sticky feel due to wetting back of a water-based liquid under load, or other unpleasant feels to the user wearing the product. A dry feel, although variable from user to user, is basically realized if, when the product is worn, the humidity between the body and the absorbing product (internal humidity when worn) is low (a barely noticeable humid feel) and the wet back is low (a barely noticeable sticky feel). Low humidity between the body and the absorbing product is, for example, 70% or less, more preferably 65% or less, in the evaluation (detailed later).

Preferable ranges of the internal humidity when worn and the wet back are specified suitably to match the kind, shape, etc. of absorbing product and not limited in any particular manners.

The following will describe the present invention in more detail by way of examples and comparative examples in reference to FIG. 1 through FIG. 4. However, the present invention is by no means limited by the description. The absorbency under no load and absorbency under load, water-soluble components, bulk specific gravity, solid components, and weight mean particle diameter of the water-absorbing resin and its precursor; the ventilation resistance of the absorbent and the water-absorbing resin under load in a wet state; the absorbency under a 2.0 kPa load and wet back of the absorbent; and the internal humidity of the paper diaper when worn were measured as in the following description. The product was evaluated with respect to comfort by evaluators, also as in the following.

[Absorbency under No Load of Water-Absorbing Resin]

A 0.2 g water-absorbing resin or its precursor was put uniformly in a non-woven fabric bag (60 mm by 60 mm) and soaked at 23° C. in physiological salt solution (a water solution containing 0.9 weight percent sodium chloride) or artificial urine (a water solution containing 0.2 weight percent sodium sulfate, 0.2 weight percent potassium chloride, 0.05 weight percent magnesium chloride hexahydrate, 0.025 weight percent calcium chloride dihydrate, 0.085 weight percent ammonium dihydrogenphosphate, and 0.015 weight percent diammonium hydrogenphosphate). The bag was pulled out of the solution after 60 minutes and placed in a centrifugal separation at 250 G for 3 minutes to remove water. Then the bag weighed $W_1$ (g). The same operations were repeated without using the water-absorbing resin; the bag weighed $W_0$ (g). The absorbency under no load (g/g) of the water-absorbing resin (or its precursor) was calculated based on the weights $W_1$, $W_0$ and the equation:

Absorbency under No Load $(g/g)=\{(W_1(g)-W_0(g))$/Weight of Water-absorbing Resin (or its Precursor) $(g)\}-1$

[Absorbency of Water-Absorbing Resin under Load]

Now, a brief description will be given as to a measurement instrument to measure the absorbency of the water-absorbing resin under load in reference to FIG. 1.

As shown in FIG. 1, the measurement instrument included a balance 1, a container 2 having a predetermined capacity on the balance 1, an ambient air inlet pipe 3, a conduit 4, a glass filter 6, and a measurement section 5 on the glass filter 6. The container 2 had openings 2a, 2b at its top and side respectively. The ambient air inlet pipe 3 was inserted through the opening 2a, and the conduit 4 was attached to the opening 2b.

The container 2 contained a predetermined amount of physiological salt solution 12 or artificial urine (25° C.; for compositions, see "Absorbency under No Load of Water-Absorbing Resin" above), and the ambient air inlet pipe 3 submerged at its lower end in the physiological salt solution 12 or artificial urine. The glass filter 6 had been formed with a diameter of 70 mm. The container 2 was interconnected to the glass filter 6 via the conduit 4. The glass filter 6 was secured so that its top was positioned slightly higher than the lowest part of the ambient air inlet pipe 3.

The measurement section 5 included a filter paper 7, a support round cylinder 8, a metal net 9 attached to the bottom of the support round cylinder 8, and a weight 10. To assembly the measurement section 5, the filter paper 7 and the support round cylinder 8 (i.e., metal net 9) were placed in this sequence on the glass filter 6, and the weight 10 was placed inside the support round cylinder 8, i.e., on the metal net 9. The support round cylinder 8 was formed with an inner diameter of 60 mm. The metal net 9 had been made of stainless steel with 400 mesh (the mesh measures 38 µm). On the metal net 9 was uniformly scattered a predetermined amount of water-absorbing resin 11. The weight 10 was adjusted in weight so as to uniformly apply loads of 4.9 kPa and 2.0 kPa to the metal net 9, i.e., the water-absorbing resin 11.

The absorbency under load of the water-absorbing resin 11 was measured using the measurement instrument with this arrangement. Now, a measurement method will be described.

Predetermined preparatory operations were done first, including putting predetermined amounts of the physiological salt solution 12 or artificial urine in the container 2 and inserting the ambient air inlet pipe 3 in the container 2. Next, the filter paper 7 was placed on top of the glass filter 6. Concurrently with these assembly operations, 0.9 g of the water-absorbing resin 11 was scattered inside the support round cylinder 8, i.e., on the metal net 9, and the weight 10 was placed on the water-absorbing resin 11.

Starting at the time when the support round cylinder 8 is placed on the filter paper 7, the weight, $W_2$ (g), of the physiological salt solution 12 or artificial urine absorbed by the water-absorbing resin 11 over the 60 minute period was measured using the balance 1.

Thereafter, the absorbency under load (g/g) 60 minutes into the absorption was calculated based on the weight $W_2$ and the equation:

Absorbency under Load $(g/g)$=Weight $W_2(g)$/Weight of Water-absorbing resin $(g)$

[Water-Soluble Components in Water-Absorbing Resin]

0.500 g of a water-absorbing resin or its precursor was dispersed in 1000 ml of deionized water and stirred for 16 hours at 23° C. before filtering with filter paper. 50 g of the filtered liquid was put in a 100 ml beaker, and 1 ml of a 0.1 mole/l water solution of sodium hydroxide, 10.00 ml of a water solution of N/200-methyl glycol chitosan, and four drops of 0.1 weight percent water solution of toluidine blue were added to the liquid in the beaker. Colloidal titration was carried out on the liquid in the beaker with a water solution of N/400-polyvinyl potassium sulfate. The titrated was stopped when the solution turned from blue to reddish violet and the titration amount, A ml, was calculated. An identical process was repeated on 50 g of deionized water instead of 50 g of filtered liquid; the resulting titration amount was B ml.

From these titration amounts A ml and B ml, the amount of the water-soluble components (weight percent) in the water-absorbing resin (or its precursor) was given by:

Amount of Water-Soluble Component (weight percent)=$(B-A)\times 0.01\times(72\times(100-C)+94\times C)/100$ where C (mole percent) is the neutralization ratio of the acrylic acid used in the manufacture of the water-absorbing resin.

[Bulk Specific Gravity of Water-Absorbing Resin]

The bulk specific gravity was measured using a bulk specific gravity measurement instrument (manufactured by Kuramochi Scientific Instrument) in line with JIS K 3362. Specifically, in a room at 25° C.±2° C. in temperature and not less than 30% and not more than 50% in relative humidity, 120 g of a water-absorbing resin or its precursor were put in a funnel with a damper closed, and the damper was opened immediately to put a sample in a vessel (100 ml). After scraping the heaped portion of the sample off the vessel using a glass bar, the vessel was weighed in grams with the remaining sample in it to a 0.1 g precision, and the bulk specific gravity was calculated in g/ml.

[Solid Components in Water-Absorbing Resin]

1.000 g of the water-absorbing resin or its precursor obtained from the dried polymer was put in an aluminum cup (measuring 53 mm in inner diameter and 23 mm in height) and dried again for 3 hours at 180° C. in an windless oven. The amount of solid components in the water-absorbing resin (or its precursor) was calculated in weight percent from the drying loss in grams.

[Weight Mean Particle Diameter of Water-absorbing Resin]

The water-absorbing resin or its precursor particles were classified using JIS Standard sieves (850 µm, 600 µm, 300 µm, 150 µm, and 106 µm), and the particles were weighed for each size (larger than 850 μm, 850 μm to 600 μm, 600 μm to 300 μm, 300 μm to 150 μm, 150 μm to 106 μm, and smaller than 106 μm). Additional JIS Standard sieves were also used when necessary. Results were plotted to draw a particle size distribution on a logarithmic probability sheet to obtain a weight mean particle diameter (D50).

[Ventilation Resistance of Absorbent under Load in Wet State]

Figure 2:
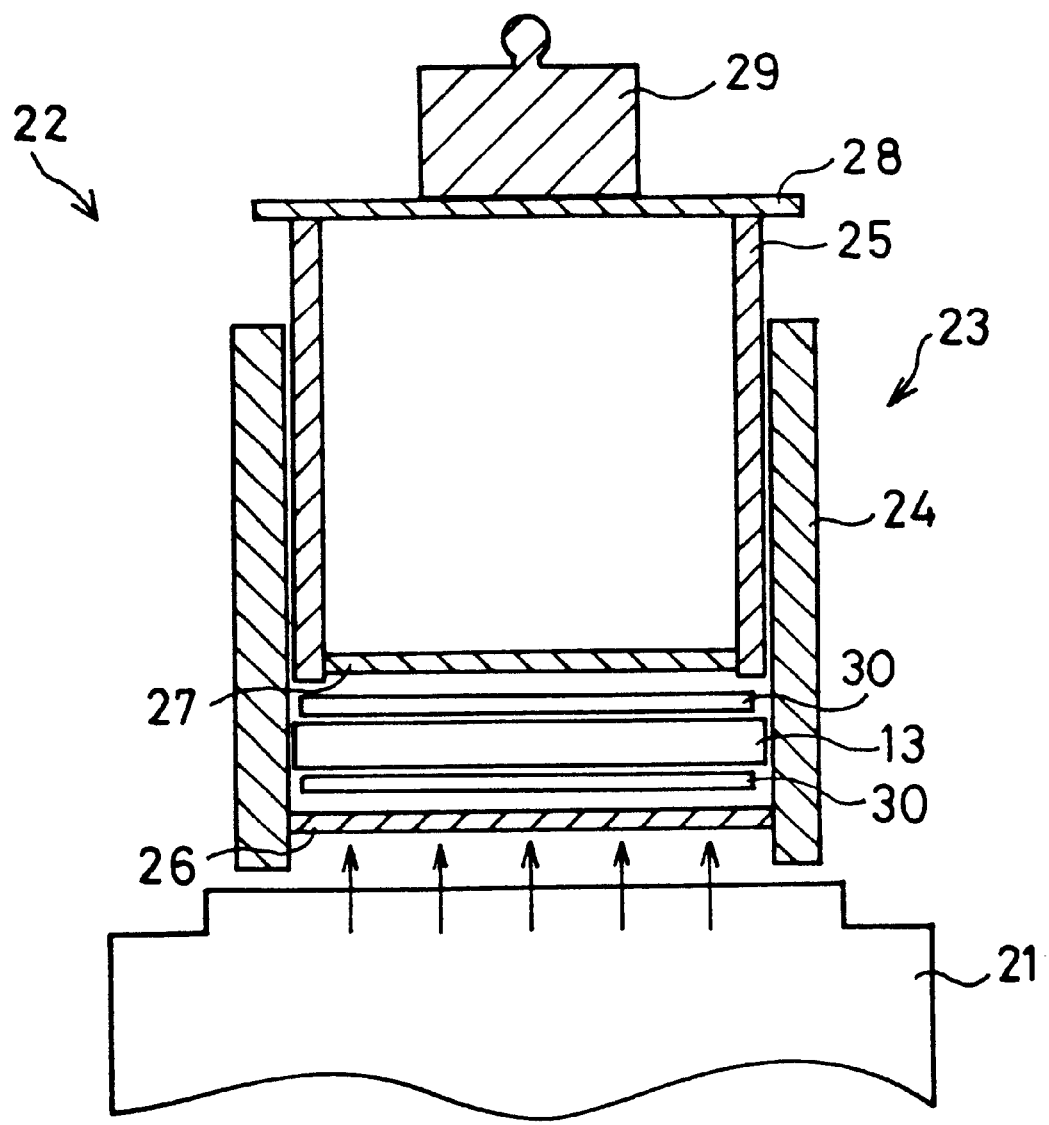
FIG. 2 is a cross-sectional view schematically showing an arrangement of a measurement instrument for ventilation resistance, one of performances of the absorbent and water-absorbing resin in accordance with the present invention.

The ventilation resistance of the absorbent was measured using a ventilating properties evaluation instrument (KES-F8-AP1, Kato Tech. Co., Ltd., Minami Ward, Kyoto City, Japan). Referring to FIG. 2, a brief description will be given below to a cell section where the absorbent to be measured on is placed.

As shown in FIG. 2, the cell section 22 where the absorbent 13 was placed included a cell set 23 inside which the absorbent 13 to be measured on was placed, a weight 29 on top of the cell, and a metal net 28 with 9 mm openings on which the weight 29 was placed. The cell set 23 was constructed of a cylindrical outer cell 24 (89.5 mm in inner diameter) and inner cell 25 (89.2 mm in outer diameter). Metal nets 26, 27 with 7 mm openings were fixed to the bottoms of the outer cell 24 and the inner cell 25 respectively. The outer cell 24 and the inner cell 25 were peripheral parts of the ventilating properties evaluation instrument 21 (available from Kato Tech. Co., Ltd.).

The weight 29 was adjusted in weight so as to uniformly apply a load of 4.9 kPa to the metal net 27 on the bottom of the inner cell 25, i.e., the absorbent 13.

The ventilating properties under load were measured using the measurement instrument arranged as above and designated as the ventilation resistance R (kPa·sec/m) under a load of 4.9 kPa. The value of the ventilation resistance R was indicative of whether or not the sample possessed satisfactory ventilation. The ventilation resistance R was relatively small if the absorbent had satisfactory ventilating properties and was relatively large if the absorbent had unsatisfactory ventilating properties. A method of measuring the ventilation resistance R will be described below.

In the present example, measurement of the ventilation resistance R was performed in a thermostatic, humidity static chamber at a temperature of 23° C. and a humidity of 65% RH.

To measure the ventilation resistance R, a piece of the non-woven fabric 30 (Heatron Paper GS-22 available from Nangoku Pulp Industries, Co., Ltd.) that had been cut out with an 89.4 mm diameter was placed on top and bottom of a piece of the absorbent 13 that was cut out with an 89.4 mm diameter and before being put in the outer cell 24. The inner cell 25 is then inserted inside the outer cell 24. On top of the inner cell 25 was placed the metal net 28, followed by the weight 29.

40 g of 23° C. physiological salt solution, prepared in advance, was poured over the absorbent 13 under load that was explained above and left still for 30 minutes, before the cell section 22 was attached to the ventilating properties evaluation instrument 21 to measure the ventilation resistance R. The speed of the reciprocal motion of the cylinder inside the ventilating properties evaluation instrument 21 during measurement was specified to 2 cm/sec.

The ventilation resistance R was measured using a mechanism in which the cylinder, provided inside the ventilating properties evaluation instrument 21, reciprocally moved to pump a static air flow to the sample (represented by arrows in the figure), discharge air through the sample, and then pull in air. In the mechanism, pressure loss due to the sample was measured within one cycle or 10 seconds, using semiconductor pressure difference gauge. Therefore, the ventilation resistance R of the sample could be read directly on the digital panel meter.

When the basis weight of the absorbent varied from place to place in a single diaper, the absorbent was cut out in a substantially circular piece of 89.4 mm in diameter that encompasses the portion of the diaper where the basis weight is maximum, and the ventilation resistance was measured on that piece (with the top and back sheets removed).

The ventilation resistance of the liquid impermeable sheet was measured by the same method as that of the absorbent, except that measurement was performed on a piece, measuring 89.4 mm in diameter, of liquid impermeable sheet that had been cut out from a diaper and dried.

[Ventilation Resistance of Water-Absorbing Resin under Load in Wet State]

The ventilation resistance of the water-absorbing resin was measured using the ventilating properties evaluation instrument (KES-F8-AP1, Kato Tech. Co., Ltd.) mentioned in the section "Ventilation Resistance of Absorbent under Load in Wet State." Therefore, the following will describe only what is different from the foregoing procedure, in reference to FIG. 2.

First, to measure the ventilation resistance of the water-absorbing resin under a 4.9 kPa load in a wet state, 2 g of the water-absorbing resin was put in 30 g of physiological salt solution for 30 minutes to swell (23° C.). Thereafter, a nylon mesh sheet cut out with an 89.4 mm diameter (305 μm openings) was put in the outer cell 24 and the swelled water-absorbing resin was scattered over the mesh sheet. Another mesh sheet cut out with an 89.4 mm diameter was placed the scattered resin before inserting the inner cell 25 in the outer cell 24. On top of the inner cell 25 was placed the metal net 28, followed by the weight 29. After placing the weight 29, the whole system was left still for 3 minutes, before the cell section 22 was attached to the ventilating properties evaluation instrument 21 to measure the ventilation resistance R. The speed of the reciprocal motion of the cylinder inside the ventilating properties evaluation instrument 21 during measurement was specified to 2 cm/sec.

[Absorbency of Absorbent under 2.0 kPa Load]

A brief description will be given as to a measurement instrument to measure the absorbency of the absorbent under load in reference to FIGS. 3 and 4.

Figure 3:
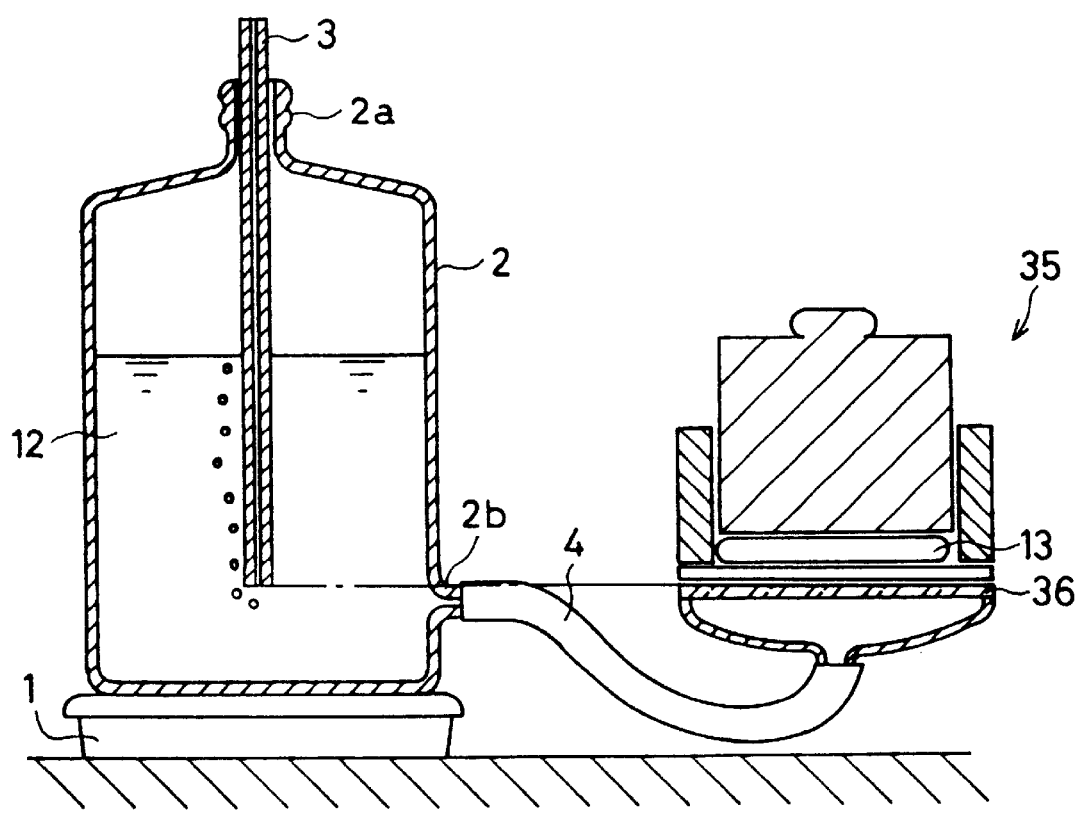
FIG. 3 is a cross-sectional view schematically showing an arrangement of a measurement instrument for absorbency under load, one of performances of the absorbing product in accordance with the present invention.

As shown in FIG. 3, the measurement instrument included a balance 1, a container 2, an ambient air inlet pipe 3, a conduit 4, a glass filter 36 measuring 20 mm in diameter, and a measurement section 35 on the glass filter 36. The container 2 had the same arrangement as the one described in "Absorbency of Water-absorbing resin under Load," and therefore detailed description thereof is omitted. The container 2 contained the physiological salt solution 12 (23° C.) in it.

Figure 4:
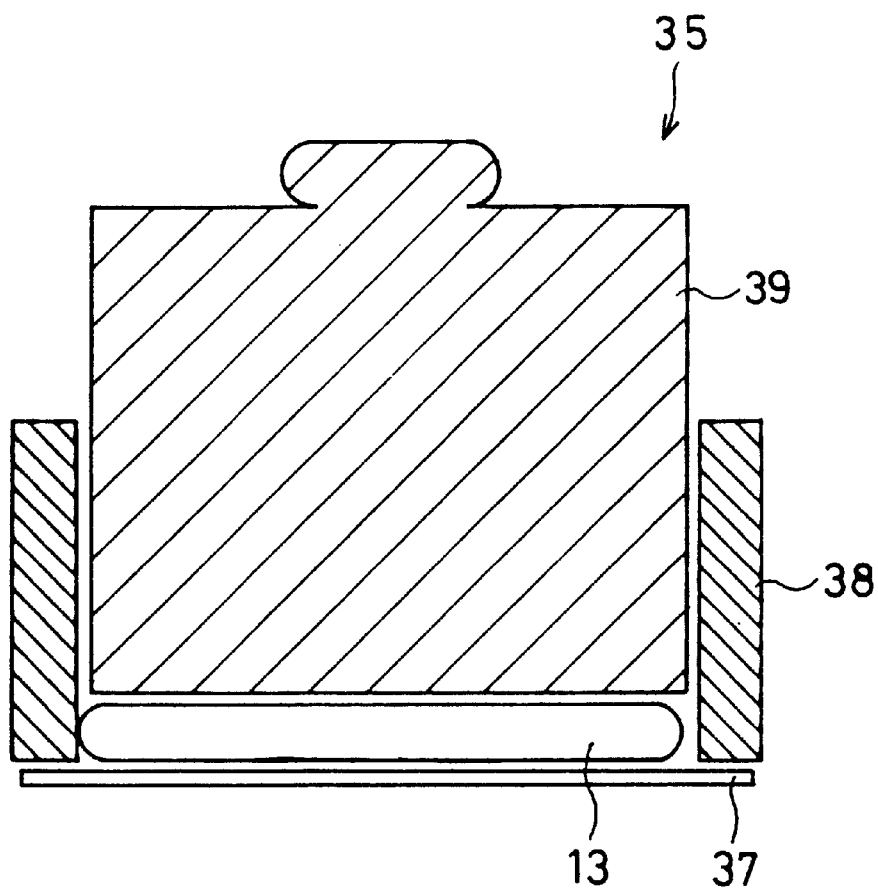
FIG. 4 is a cross-sectional view schematically showing an arrangement of a measurement section in the measurement instrument in FIG. 3.

The measurement section 35, as shown in FIG. 4, included a filter paper 37, a support cornered cylinder 38, and a weight 39. To assembly the measurement section 35, the filter paper 37 and the support cornered cylinder 38 were placed in this sequence on the glass filter 36, and the weight 39 was placed inside the support cornered cylinder 38. The support cornered cylinder 38 was formed with inner dimensions of 100 mm by 100 mm, and the absorbent 13 of predetermined dimensions is placed right under the weight 39 in the support cornered cylinder 38.

The absorbency under load of the absorbent 13 was measured using the measurement instrument with this arrangement. Now, a measurement method will be described.

First, the absorbent 13 was fabricated with dimensions 100 mm by 100 mm. Predetermined preparatory operations were done similarly as described in "Absorbency of Water-absorbing resin under Load." Next, the filter paper 37 was placed on top of the glass filter 36, and then the support cornered cylinder 38 was placed so that its center is right above the center of the glass filter 36. Thereafter, the absorbent 13 of predetermined dimensions was placed inside the support cornered cylinder 38, and the weight 39 was placed on the absorbent 13. The weight 39 was adjusted in weight so as to uniformly apply a load of 2.0 kPa to the absorbent 13. Note that the absorbent 13 and the weight 39 were put in place very quickly.

Starting at the time when the absorbent 13 is placed on the filter paper 37, the weight, $W_3$ (g), of physiological salt solution absorbed by the absorbent 13 over the 60 minute period was measured using the balance 1.

The absorbency under load (g/g) of the absorbent 13 at 60 minutes into the absorption was calculated based on the weight $W_3$ and the equation:

Absorbent's Absorbency under Load $(g/g)$=Weight $W_3(g)$/Absorbent's Weight $(g)$ When the basis weight of the absorbent varied from place to place in a single diaper, the absorbent was cut out in a substantially square piece of 100 mm by 100 mm that encompasses the portion of the diaper where the basis weight is maximum, and the absorbency under load was measured on that piece (with the top and back sheets removed).

[Wet Back of Absorbent]

120 g of physiological salt solution (23° C.) was poured over a cut-out piece of absorbent measuring 100 mm by 100 mm, and the piece was left for 60 minutes. Fifteen stacked sheets of Nepia (TM) cooking towel (Oji Paper Co., Ltd.) was folded in half, and the weight, $W_4$ (g), of the cooking towel was measured. The stacked sheets were placed on top of the absorbent, and a 10 kg weight was placed on the absorbent. Then, the weight $W_5$ (g) of the cooking towel removed from the top of the absorbent was measured. The wet back (g) was calculated based on the weights $W_4$, $W_5$, and the equation Wet Back $(g)$=Weight $W_5(g)$−Weight $W_4(g)$

[Internal Humidity of Absorbing Product When Worn]

First, a paper diaper (absorbing product) to be measured on was fabricated as follows.

A water-absorbing resin was dried and mixed with ground wood pulp in a mixer. Then, the mixture was subjected to a batch-type air paper making machine to form a web on a wire screen with 400 mesh (the mesh measured 38 μm). The web was then pressed at 2 kg/cm² (196 kPa) for 5 seconds to obtain absorbent.

Next, a back sheet (liquid impermeable sheet) of liquid impermeable polypropylene with "leg gathers," the absorbent, and a top sheet (liquid permeable sheet) of liquid permeable polypropylene were adhered together in this sequence using double-sided adhesive tape. Two "tape fastener" were then attached to the adhered body to obtain a paper diaper (absorbing product).

The liquid impermeable sheet used for the paper diaper had a ventilation resistance of 24 kPa·sec/m.

The paper diaper was worn on a plastics doll that measured 55 cm in height and weighed 5 kg. The doll had humidity sensors (ThermoHygrosensors: Model THP-14) attached to its crotch and way back to buttocks to allow measurement of variations of humidity with time.

The doll in a paper diaper was laid prone. A tube was placed between the paper diapers and the doll. 50 ml of physiological salt solution (23° C.) was poured where a human body would discharges urine, and the doll was left for 30 minutes before measuring humidity in the paper diaper worn on the doll.

Readings on a data stocker (THR-DM2: available from SHINYEI) coupled to the humidity sensors were recorded as the internal humidity when worn.

[Evaluation of Absorbing Product]

The product was evaluated by adult evaluators wearing paper diapers (absorbing product) designed for adults. The paper diapers used in the evaluation was prepared in the following manner.

First, an absorbing resin was dried and mixed with ground wood pulp in a mixer. Then, the mixture was subjected to a batch-type air paper making machine to form a web measuring 200 mm by 700 mm on a wire screen with 400 mesh (the mesh measured 38 μm). The web was then pressed at 2 kg/cm² (196 kPa) for 5 seconds to obtain absorbent.

Next, a back sheet (liquid impermeable sheet) of liquid impermeable polypropylene with "leg gathers," the absorbent, and a top sheet (liquid permeable sheet) of liquid permeable polypropylene were adhered in this sequence using double-sided adhesive tape. Two "tape fastener" were then attached to the adhered body to obtain a paper diaper (absorbing product).

The prepared paper diapers were evaluated with respect to comfort in the diaper, by ten evaluators observing whether he/she had a humid/sticky feel in the diaper after urinating once.

EXAMPLE 1

Polyethylene glycol diacrylate (mean number of attached ethylene oxides in moles: 8) was dissolved at 0.035 mole percent in a 5,500 g water solution of sodium acrylate (concentration of monomer: 35 weight percent) having a neutralization ratio of 75 mole percent, to prepare a reaction liquid. The reaction liquid was then degassed under a nitrogen atmosphere for 30 minutes.

The reaction liquid was then introduced in a reaction container so that the air in the system was replaced for a nitrogen gas, while keeping the reaction liquid at 20° C. The reaction container was constructed by attaching a lid to a stainless steel twin-arm kneader having a 10-litter-capacity jacket with two sigma blades. Subsequently, 3.5 g of sodium persulfate and 0.02 g of L-ascorbic acid were added while stirring the reaction liquid. Polymerization started about 1 minute after the addition and continued at 20° C. to 90° C. A water-containing gel-like polymer was obtained 60 minutes into the polymerization.

The obtained water-containing gel-like polymer were divided into small pieces of about 5 mm in diameter. The finely divided water-containing gel-like polymer was spread on a 50 mesh metal net (300 μm openings) and dried with heated air of 170° C. for 60 minutes. The dried article was ground using a vibration mill and classified using a 20 mesh metal net (850 μm openings). Classification was continued further so that ground particles less than 106 μm in diameter would account for 5 weight percent or less, to obtain randomly crushed water-absorbing resin precursor (a) that exhibited a bulk specific gravity of 0.68 g/ml and that was 98 weight percent solid. Water-absorbing resin precursor (a), when having absorbed physiological salt solution, exhibited an absorbency under no load of 40 g/g and contained 13 weight percent water-soluble components.

A surface crosslinking agent (30° C.) that was 1 part by weight 1,4-butanediol, 0.05 parts by weight ethylene glycol glycidyl ether, 2 parts by weight water, and 1 part by weight ethanol was mixed to 100 parts by weight (70° C.) of resultant water-absorbing resin precursor (a). The obtained mixture was subjected to a heat treatment at 195° C. for 50 minutes to obtain water-absorbing resin (1) that had a weight mean particle diameter of 450 μm. Those particles measuring less than 106 μm in diameter accounted for 2 weight percent or less of water-absorbing resin (1). Measurements of the absorbency under no load and under load, amounts of water-soluble components, weight mean particle diameter, and ventilation resistance of water-absorbing resin (1) are shown in Table 1.

EXAMPLE 2

A water-containing gel-like polymer was derived by the same process of polymerization as in example 1 except that the reaction liquid was prepared by dissolving a 0.03 mole percent N,N'-methylene-bisacrylamide in 5,500 g of a water solution of sodium acrylate (monomer concentration: 35 weight percent) having a neutralization ratio of 75 mole percent. The resultant water-containing gel-like polymer was ground and classified by the same process as in example 1 to obtain randomly crushed water-absorbing resin precursor (b) that exhibited a bulk specific gravity of 0.68 g/ml and that was 97 weight percent solid. Water-absorbing resin precursor (b), when having absorbed physiological salt solution, exhibited an absorbency under no load of 48 g/g and contained 16 weight percent water-soluble components.

A surface crosslinking agent (28° C.) that was 1 part by weight-propylene glycol, 0.05 parts by weight ethylene glycol glycidyl ether, 2 parts by weight water, and 1 part by weight ethanol was mixed with 100 parts (75° C.) by weight of resultant water-absorbing resin precursor (b). The mixture was subjected to a heat treatment at 200° C. for 40 minutes to obtain water-absorbing resin (2) that had a weight mean particle diameter of 500 μm. Those particles measuring less than 106 μm in diameter accounted for 1 weight percent or less of water-absorbing resin (2). Measurements of the absorbency under no load and under load, amounts of water-soluble components, weight mean particle diameter, and ventilation resistance of water-absorbing resin (2) are shown in Table 1.

Comparative Example 1

A dried product of the water-containing gel-like polymer prepared by the same process as in example 1 was ground using a vibration mill and classified using a 20 mesh metal net (850 μm openings) to obtain randomly crushed water-absorbing resin precursor (c) that exhibited a bulk specific gravity of 0.71 g/ml and that was 98 weight percent solid. Water-absorbing resin precursor (c), when having absorbed physiological salt solution, exhibited an absorbency under no load of 39 g/g and contained 13 weight percent water-soluble components.

A surface crosslinking agent (35° C.) that was 1 part by weight propylene glycol, 0.03 parts by weight ethylene glycol diglycidyl ether, 3 parts by weight water, and 1 part by weight ethanol was mixed with 100 parts by weight (65° C.) of resultant water-absorbing resin precursor (c). The mixture was subjected to a heat treatment at 210° C. for 60 minutes to obtain water-absorbing resin (3) that had a weight mean particle diameter of 310 μm. Those particles measuring less than 106 μm in diameter accounted for 6 weight percent of water-absorbing resin (3). Measurements of the absorbency under no load and under load, amounts of water-soluble components, weight mean particle diameter, and ventilation resistance of water-absorbing resin (3) are shown in Table 1.

Comparative Example 2

A water-containing gel-like polymer was derived by the same process of polymerization as in example 1 except that 5,500 g of a water solution of sodium acrylate (monomer concentration: 39 weight percent) having a neutralization ratio of 71.3 mole percent was used instead of that of example 1. Then, the water-containing gel-like polymer was dried and ground by the same drying and classification process as in example 1, except that the polymer was dried with heated air of 170° C. for 70 minutes, to obtain randomly crushed water-absorbing resin precursor (d) that exhibited a bulk specific gravity of 0.67 g/ml and that was 98 weight percent solid. Water-absorbing resin precursor (d), when having absorbed physiological salt solution, exhibited an absorbency under no load of 31 g/g and contained 7 weight percent water-soluble components.

A surface crosslinking agent (20° C.) that was 0.5 parts by weight propylene glycol, 0.5 parts by weight 1,4-butanediol, 3 parts by weight water, and 0.5 parts by weight isopropyl alcohol was mixed with 100 parts by weight (78° C.) of resultant water-absorbing resin precursor (d). The mixture was subjected to a heat treatment at 210° C. for 30 minutes to obtain water-absorbing resin (4) that had a weight mean particle diameter of 430 μm. Those particles measuring less than 106 μm in diameter accounted for 3 weight percent of water-absorbing resin (4). Measurements of absorbency under no load and under load, amounts of water-soluble components, weight mean particle diameter, and ventilation resistance of water-absorbing resin (4) are shown in Table 1.

Comparative Example 3

A dried product of the water-containing gel prepared by the same process as in example 2 was ground using a vibration mill and classified using a 20 mesh metal net to obtain randomly crushed water-absorbing resin precursor (e) that exhibited a bulk specific gravity of 0.68 g/ml and that was 98 weight percent solid. Water-absorbing resin precursor (e), when having absorbed physiological salt solution, exhibited an absorbency under no load of 48 g/g and contained 16 weight percent water-soluble components.

A surface crosslinking agent (25° C.) that was 0.5 parts by weight glycerol, 1 part by weight water, and 1 part by weight ethanol was mixed with 100 parts by weight (80° C.) of resultant water-absorbing resin precursor (e). The mixture was subjected to a heat treatment at 195° C. for 30 minutes to obtain water-absorbing resin (5) that had a weight mean particle diameter of 480 μm. Those particles measuring less than 106 μm in diameter accounted for 2 weight percent of water-absorbing resin (5). Measurements of the absorbency under no load and under load, amounts of water-soluble components, weight mean particle diameter, and ventilation resistance of water-absorbing resin (5) are shown in Table 1.

EXAMPLE 3

A water-containing gel-like polymer was derived by the same process of polymerization as in example 1 except that the reaction liquid was prepared by dissolving a 0.07 mole percent polyethylene glycol diacrylate (mean number of attached ethylene oxides in moles: 9) in 5,500 g of a water solution of sodium acrylate (monomer concentration: 38 weight percent) having a neutralization ratio of 75 mole percent. The resultant water-containing gel-like polymer was ground and classified by the same process as in example 1 to obtain randomly crushed water-absorbing resin precursor (f) that exhibited a bulk specific gravity of 0.67 g/ml and that was 97 weight percent solid. Water-absorbing resin precursor (f), when having absorbed physiological salt solution, exhibited an absorbency under no load of 38 g/g and contained 14 weight percent water-soluble components.

A surface crosslinking agent (35° C.) that was 0.5 parts by weight 1,4-butanediol, 0.5 parts by weight propylene glycol, and 4.0 parts by weight water was mixed with 100 parts (70° C.) by weight of resultant water-absorbing resin precursor (f). The mixture was subjected to a heat treatment at 199° C. for 30 minutes to obtain water-absorbing resin (6) that had a weight mean particle diameter of 550 μm. Those particles measuring less than 106 μm in diameter accounted for 1 weight percent of water-absorbing resin (6). Measurements of the absorbency under no load and under load, amounts of water-soluble components, weight mean particle diameter, and ventilation resistance of water-absorbing resin (6) are shown in Table 1.

EXAMPLE 4

0.01 parts by weight silicon dioxide was added to 100 parts by weight of water-absorbing resin (1) prepared in embodiment 1 to obtain water-absorbing resin (7). Measurements of the absorbency under no load and under load, amounts of water-soluble components, weight mean particle diameter, and ventilation resistance of water-absorbing resin (7) are shown in Table 1.

Tables 2 and 3. Measurements of the internal humidity and evaluations with respect of comfort of absorbing product (1) when it was being worn are shown in Table 2.

EXAMPLE 6

Absorbent (2), and hence absorbing product (2), were prepared by the same process as in example 5 except that water-absorbing resin (2) obtained in example 2 was used instead of water-absorbing resin (1) as in example 5. Absorbing product (2) made here weighed 44 g.

The ventilation resistance, absorbency under load, and wet back of absorbent (2) and the internal humidity of absorbing product (2) when it was being worn were measured by the same process as in example 5. Absorbing product (2) was evaluated with respect to comfort by evaluators, also by the same process as in example 5.

Results are shown in Table 2.

Comparative Example 4

Absorbent (3), and hence absorbing product (3), were prepared by the same process as in example 5 except that water-absorbing resin (3) obtained in comparative example 1 was used instead of water-absorbing resin (1) as in example 5. Absorbing product (3) made here weighed 44 g.

The ventilation resistance, absorbency under load, and wet back of absorbent (3) and the internal humidity of absorbing product (3) when it was being worn were mea-

TABLE 1

| | | | Water-Absorbing Resins | | | | |
|---|---|---|---|---|---|---|---|
| Examples (Comparative Examples) | Water-Absorbing Resins Used | Absorbency under no load (g/g) | Absorbency under load (g/g) | | | Water-Soluble Components (weight %) | Weight Mean Particle Diameter (μm) | Ventilation Resistance under Load In Wet State (kPa · sec/m) 4.9 kPa |
| | | PSS AU | 2.0 kPa PSS | 4.9 kPa PSS AU | | | |

| Examples | Resin | PSS | AU | PSS | PSS | AU | (weight %) | (μm) | 4.9 kPa |
|---|---|---|---|---|---|---|---|---|---|
| Ex. 1 | (1) | 36 | 45 | 34 | 26 | 34 | 13 | 450 | 47 |
| Ex. 2 | (2) | 38 | 47 | 36 | 28 | 35 | 14 | 500 | 42 |
| Com. Ex. 1 | (3) | 35 | 44 | 35 | 26 | 33 | 15 | 310 | *Unmeasurable |
| Com. Ex. 2 | (4) | 28 | 36 | 30 | 25 | 31 | 7 | 430 | 48 |
| Com. Ex. 3 | (5) | 48 | 61 | 23 | 8 | 9 | 15 | 480 | *Unmeasurable |
| Ex. 3 | (6) | 34 | 41 | 32 | 25 | 32 | 14 | 550 | 39 |
| Ex. 4 | (7) | 35 | 44 | 33 | 25 | 33 | 13 | 450 | 35 |

PSS < Physiological Salt Solution
AU < Artificial Urine
*Unmeasurable because the ventilation resistance is too great.

EXAMPLE 5

75 parts by weight of absorbing resin (1) obtained in example 1 was dried and mixed with 25 parts by weight of ground wood pulp in a mixer. Then, the mixture was subjected to a batch-type air paper making machine to form a web measuring 120 mm by 350 mm on a wire screen with 400 mesh (the mesh measured 38 μm). The web was then pressed at 2 kg/cm² (196 kPa) for 5 seconds to obtain absorbent (1) with a basis weight of about 500 g/cm². Absorbent (1) was further fabricated into absorbing product (1) (paper diaper) that weighed 44 g.

Measurements of the ventilation resistance, absorbency under load, and wet back of absorbent (1) are shown in sured by the same process as in example 5. Absorbing product (3) was evaluated with respect to comfort by evaluators, also by the same process as in example 5.

Results are shown in Table 2.

Comparative Example 5

Absorbent (4), and hence absorbing product (4), were prepared by the same process as in example 5 except that water-absorbing resin (4) obtained in comparative example 2 was used instead of water-absorbing resin (1) as in example 5. Absorbing product (4) made here weighed 44 g.

The ventilation resistance, absorbency under load, and wet back of absorbent (4) and the internal humidity of absorbing product (4) when it was being worn were measured by the same process as in example 5. Absorbing product (4) was evaluated with respect to comfort by evaluators, also by the same process as in example 5.

product (7) was evaluated with respect to comfort by evaluators, also by the same process as in example 5.

Results are shown in Table 2.

TABLE 2

| | | Absorbent | | | Absorbing Product | |
|---|---|---|---|---|---|---|
| Examples | Water-Absorbing | Ventilation Resistance under Load in Wet State | Absorbency under 2.0 | | | |
| (Comparative Examples) | Resins Used | (kPa · sec/m) 4.9 kPa | kPa load (g/g) | Wet Back (g) | Humidity (%) | Comfort Evaluation |
| Ex. 5 | (1) | 40 | 26 | 9 | 66 | Good |
| Ex. 6 | (2) | 30 | 28 | 8 | 64 | Good |
| Com. Ex. 4 | (3) | 107 | 25 | 9 | 71 | Humid |
| Com. Ex. 5 | (4) | 17 | 22 | 15 | 66 | Sticky |
| Com. Ex. 6 | (5) | 122 | 18 | 10 | 80 | Humid |
| Ex. 7 | (6) | 29 | 25 | 12 | 65 | Good |
| Ex. 8 | (7) | 25 | 26 | 10 | 64 | Good |

Results are shown in Table 2.

Comparative Example 6

Absorbent (5), and hence absorbing product (5), were prepared by the same process as in example 5 except that water-absorbing resin (5) obtained in comparative example 5 was used instead of water-absorbing resin (1) as in example 5. Absorbing product (5) made here weighed 44 g.

The ventilation resistance, absorbency under load, and wet back of absorbent (5) and the internal humidity of absorbing product (5) when it was being worn were measured by the same process as in example 5. Absorbing product (5) was evaluated with respect to comfort by evaluators, also by the same process as in example 5.

Results are shown in Table 2.

EXAMPLE 7

Absorbent (6), and hence absorbing product (6), were prepared by the same process as in example 5 except that water-absorbing resin (6) obtained in example 3 was used instead of water-absorbing resin (1) as in example 5. Absorbing product (5) made here weighed 44 g.

The ventilation resistance, absorbency under load, and wet back of absorbent (6) and the internal humidity of absorbing product (6) when it was being worn were measured by the same process as in example 5. Absorbing product (6) was evaluated with respect to comfort by evaluators, also by the same process as in example 5.

Results are shown in Table 2.

EXAMPLE 8

Absorbent (7), and hence absorbing product (7), were prepared by the same process as in example 5 except that water-absorbing resin (7) obtained in example 4 was used instead of water-absorbing resin (1) as in example 5. Absorbing product (7) made here weighed 44 g.

The ventilation resistance, absorbency under load, and wet back of absorbent (7) and the internal humidity of absorbing product (7) when it was being worn were measured by the same process as in example 5. Absorbing

[Comparative Water-Absorbing Resin and Comparative Absorbent]

Absorbents were extracted from ten absorbing products (paper diapers) available on the market and used as comparative absorbents in comparative examples 17 to 26 detailed below. Further, water-absorbing resins were separated from these absorbents and used as comparative water-absorbing resins in comparative examples 7 to 16 detailed below. Table 3 identifies the absorbing products by their commercial names and manufactures, the manufactures' nationalities, and the purchasing dates.

Comparative Examples 7–16

The absorbency under no load and under load, amounts of water-soluble components, weight mean particle diameter, and ventilation resistance of the ten comparative water-absorbing resins were measured by the same process as in embodiment 1. Results are shown in Table 4.

Comparative Examples 17–26

The ventilation resistance, absorbency under load, and wet back of the ten comparative absorbents were measured by the same process as in embodiment 5. Comparative absorbing products were fabricated back from the comparative absorbents and evaluated with respect to comfort by evaluators, all by the same process as in example 5. The internal humidity of the comparative absorbing products when they were being worn were measured also by the same process as in example 5. Results are shown in Table 5. Also shown in Table 5 are the ventilation resistances of the liquid impermeable sheets (back sheets) of the absorbing products available on the market.

TABLE 3

| Comparative Absorbents Used | Water-Absorbing Resins Used | Commercial Names of Absorbing Products | Manufacturer/ Nationality | Date Purchased |
|---|---|---|---|---|
| (a) | (a) | Pampers Sarasara Care | P&G/Japan | Oct. 1998 |
| (b) | (b) | Doremi fain | Oji Paper/Japan | Mar. 2000 |
| (c) | (c) | Super Melize | Kao/Japan | Oct. 1998 |
| (d) | (d) | Libero UP&GO | Molntcke/Sweden | Mar. 1998 |
| (e) | (e) | Fixies Extraclass | Hartmann/Germany | May. 1998 |
| (f) | (f) | Luvs Ultra Leakguards | P&G/USA | Jun. 1999 |
| (g) | (g) | Pampers Premium | P&G/USA | Jun. 1999 |
| (h) | (h) | Huggies Overnites | Kimberley-Clark/USA | Jun. 1999 |
| (i) | (i) | Huggies Ultratrim | Kimberley-Clark/USA | Jun. 1999 |
| (j) | (j) | Huggies Supreme | Kimberley-Clark/USA | Jun. 1999 |

TABLE 4

| | | Water-Absorbing Resins | | | | | | |
|---|---|---|---|---|---|---|---|---|
| Comparative Examples | Water-Absorbing Resins Used | Absorbency under no load (g/g) | | Absorbency under load (g/g) | | | Water-Soluble Components (weight %) | Weight Mean Particle Diameter (μm) | Ventilation Resistance under Load In Wet State (kPa · sec/m) 4.9 kPa |
| | | PSS | AU | 2.0 kPa PSS | 4.9 kPa PSS | AU | | | |
| Com. Ex. 7 | (a) | 30 | 38 | 29 | 21 | 27 | 11 | 370 | *Unmeasurable |
| Com. Ex. 8 | (b) | 30 | 37 | 30 | 18 | 23 | 10 | 380 | 10 |
| Com. Ex. 9 | (c) | 49 | 60 | 13 | 8 | 9 | 24 | 370 | *Unmeasurable |
| Com. Ex. 10 | (d) | 35 | 44 | 34 | 18 | 19 | 8 | 450 | *Unmeasurable |
| Com. Ex. 11 | (e) | 36 | 46 | 32 | 19 | 23 | 24 | 405 | *Unmeasurable |
| Com. Ex. 12 | (f) | 31 | 41 | 29 | 21 | 25 | 16 | 420 | *Unmeasurable |
| Com. Ex. 13 | (g) | 31 | 39 | 27 | 21 | 18 | 16 | 400 | *Unmeasurable |
| Com. Ex. 14 | (h) | 27 | 34 | 25 | 13 | 13 | 8 | 300 | 39 |
| Com. Ex. 15 | (i) | 28 | 35 | 23 | 11 | 12 | 9 | 320 | 91 |
| Com. Ex. 16 | (j) | 27 | 35 | 22 | 11 | 10 | 8 | 275 | *Unmeasurable |

PSS < Physiological Salt Solution
AU < Artificial Urine
*Unmeasurable because the ventilation resistance is too great.

TABLE 5

| Comparative Examples | Water-Absorbing Resins Used | Absorbent | | | | Wet Back (g) | Absorbing Product | |
|---|---|---|---|---|---|---|---|---|
| | | (i) | (ii) | (iii) | (iv) | | Humidity (%) | Comfort Evaluation |
| Com. Ex. 17 | (a) | 18 | 47 | 44 | 18 | 44 | 65 | Sticky |
| Com. Ex. 18 | (b) | 40 | 33 | *Unmeasurable | 16 | 68 | 72 | Humid, Sticky |
| Com. Ex. 19 | (c) | 24 | 41 | *Unmeasurable | 10 | 35 | 71 | Humid, Sticky |
| Com. Ex. 20 | (d) | 41 | 54 | 56 | 19 | 15 | 70 | Humid |
| Com. Ex. 21 | (e) | 49 | 32 | 11 | 14 | 12 | 65 | Good |
| Com. Ex. 22 | (f) | 29 | 42 | 72 | 15 | 69 | 71 | Humid, Sticky |
| Com. Ex. 23 | (g) | 39 | 48 | 73 | 14 | 34 | 70 | Humid, Sticky |
| Com. Ex. 24 | (h) | 30 | 39 | 12 | 13 | 11 | 65 | Good |
| Com. Ex. 25 | (i) | 13 | 39 | 11 | 15 | 28 | 66 | Sticky |
| Com. Ex. 26 | (j) | 32 | 44 | 15 | 14 | 34 | 68 | Sticky |

*Unmeasurable because the ventilation resistance is too great.
(i) Ventilation Resistance of Liquid Impermeable Sheet (kPa · sec/m)
(ii) Ratios of Water-Absorbing Resins (weight %)
(iii) Ventilation Resistance under Load in Wet State (kPa · sec/m) 4.9 kPa
(iv) Absorbency under 2.0 kPa load (g/g)

As could be understood from the tables, the water-absorbing resins, absorbents, and absorbing products with parameters that are out of the ranges specified in the present invention do not satisfy both conditions: (1) Absorbency under load must be raised to reduce wet back (elimination of a sticky feel). (2) The absorbent per se must possess improved ventilating properties (elimination of a humid feel). In contrast, the absorbents, absorbing products, and water-absorbing resins in accordance with the present invention satisfy both conditions, providing an increased sense of comfort to users wearing the absorbing products.

As detailed so far, the absorbent in accordance with the present invention is arranged so that it possesses at least sufficient ventilating properties and absorbency under load even in a wet state. Further, the absorbing product in accordance with the present invention is based on the absorbent arranged as in the foregoing. The water-absorbing resin in accordance with the present invention possesses a low ventilation resistance and a sufficient absorbency both under no load and under load and either has a weight mean particle diameter equal to a predetermined length or more or contains water-soluble components at a predetermined amount or less.

Therefore, with the arrangement of the present invention, it is ensured that the absorbent possesses sufficient ventilating properties even when the absorbent has absorbed body fluids and other water-based liquids and also that the absorbent, having absorbed a water-based liquid, sufficiently holds the liquid even under load. Therefore, the absorbent can be prevented from acting as an air-tight separation wall and thus a high humidity condition can be prevented from occurring between the body and the absorbent or the absorbing product. Increases in wet back also become preventable.

Consequently, if the absorbing product is, for example, paper diapers, the product does not give the user a humid, sticky or other unpleasant feel and continues to have a dry feel, providing an improved sense of comfort to users when they are in the absorbing product.

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

What is claimed is:

1. An absorbent of a sheet shape or a substantially cylindrical shape containing a water-absorbing resin and a fabric material, having a 24 g/g or more absorbency after 60 minutes under a 2.0 kPa load to physiological salt solution having 0.9 percent by weight of a sodium chloride aqueous solution at 23° C., and a 50 kPa·sec/m or less ventilation resistance under a 4.9 kPa load in a wet state to physiological salt solution.

2. The absorbent as defined in claim 1, comprising a 40 percent by weight or more water-absorbing resin.

3. The absorbent as defined in claim 1, having a maximum basis weight of 700 g/m² or less.

4. A water-absorbing resin having a 250 kPa·sec/m or less ventilation resistance under a 4.9 kPa load in a wet state, a 32 g/g or more absorbency under no load to physiological salt solution and a 32 g/g or more absorbency under a 2.0 kPa load to physiological salt solution, and being shaped in particles with the weighted average of the diameters of resin particles being 430 μm or more.

5. A water-absorbing resin, having a 250 kPa·sec/m or less ventilation resistance under a 4.9 kPa load in a wet state and a 34 g/g or more absorbency under no load to physiological salt solution, and comprising 18 percent by weight or less water-soluble components.

6. A water-absorbing resin, having a 250 kPa·sec/m or less ventilation resistance under a 4.9 kPa load in a wet state and a 34 g/g or more absorbency under a 2.0 kPa load to physiological salt solution, and comprising 18 percent by weight or less water-soluble components.

7. A water-absorbing resin which is produced by crosslinking a surface of water-absorbing resin precursor which contains, per 100 g, 0.01 or more equivalent amount of carboxyl groups which form a hydro gel, the water-absorbing resin being provided in particulate forms with a 250 kPa·sec/m or less ventilation resistance under a 4.9 kPa load in a wet state to physiological salt solution having 0.9 percent by weight of a sodium chloride aqueous solution at 23° C., and a 32 g/g or more absorbency after 60 minutes under a 2.0 kPa load to physiological salt solution, and the weighted average of the diameters of resin particles being 430 μm or more.

8. A water-absorbing resin, which is produced by crosslinking a surface of a water-absorbing resin precursor which contains, per 100 g of said resin precursor, 0.01 or more equivalent amount of carboxyl groups which form a hydro gel, the water-absorbing resin being provided in particulate forms with a 250 kPa·sec/m or less ventilation resistance under a 4.9 kPa load in a wet state to physiological salt solution having 0.9 percent by weight of a sodium chloride aqueous solution at 23° C., and a 34 g/g or more absorbency after 60 minutes under no load to physiological salt solution, and containing 18 percent by weight or less water-soluble components after 16 hours at 23° C.

9. A water-absorbing resin, which is produced by crosslinking a surface of water-absorbing resin precursor which contains, per 100 g of said resin precursor, 0.01 or more equivalent amount of carboxyl groups which form a hydro gel, the water-absorbing resin being provided in particulate forms with a 250 kPa·sec/m or less ventilation resistance under a 4.9 kPa load in a wet state to physiological salt solution having 0.9 percent by weight of a sodium chloride aqueous solution at 23° C, and a 34 g/g or more absorbency after 60 minutes under a 2.0 kPa load to physiological salt solution, and containing 18 percent by weight or less water-soluble components after 16 hours at 23° C.

10. An absorbent, having a 24 g/g or more absorbency under a 2.0 kPa load to physiological salt solution and a 50 kPa·sec/m or less ventilation resistance under a 4.9 kPa load in a wet state, said absorbent comprising a water-absorbing resin and a fabric material that are mixed uniformly.

11. An absorbing product, comprising:

an absorbing layer containing the absorbent as set forth in claim 1;

a liquid permeable sheet; and a liquid impermeable sheet having a ventilation resistance of not less than 1 kPa·sec/m and not more than 50 kPa sec/m, the absorbing layer being disposed between said liquid permeable sheet and said liquid impermeable sheet.

12. The absorbing product as set forth in claim 11, wherein the absorbing product is used as a sanitary material.

13. An absorbent of a sheet shape or a substantially cylindrical shape, comprising:
   the water-absorbing resin as set forth in claim 4; and
   a fabric material.

14. An absorbent of a sheet shape or a substantially cylindrical shape, comprising:
   the water-absorbing resin as set forth in claim 5, and
   a fabric material.

15. An absorbent of a sheet shape or a substantially cylindrical shape, comprising:
   the water-absorbing resin as set forth in claim 6; and
   a fabric material.

16. An absorbant of a sheet shape or a substantially cylindrical shape, comprising:
   the water-absorbing resin as set forth in claim 7; and
   a fabric material.

17. An absorbent of a sheet shape or a substantially cylindrical shape, comprising:
   the water-absorbing resin as set forth in claim 8; and
   a fabric material.

18. An absorbent of a sheet shape or a substantially cylindrical shape, comprising:
   the water-absorbing resin as set forth in claim 9; and
   a fabric material.

19. An absorbing product, comprising the absorbent as set forth in claim 13,
   wherein the water-absorbing resin contained in the absorbent accounts for not less than 40 wt. % and not more than 97 wt. %.

* * * * *